(12) United States Patent
Choi

(10) Patent No.: US 10,674,971 B2
(45) Date of Patent: Jun. 9, 2020

(54) X-RAY IMAGE DISPLAY APPARATUS AND METHOD FOR X-RAY IMAGE DISPLAY

(71) Applicants: VATECH Co., Ltd., Gyeonggi-do (KR); VATECH EWOO Holdings Co., Ltd., Gyeonggi-do (KR)

(72) Inventor: Sung Il Choi, Gyeonggi-do (KR)

(73) Assignees: VATECH Co., Ltd., Gyeonggi-do (KR); VATECH EWOO Holdings Co., Ltd., Gyeonggi-do (KR)

( * ) Notice: Subject to any disclaimer, the term of this patent is extended or adjusted under 35 U.S.C. 154(b) by 280 days.

(21) Appl. No.: 15/735,597

(22) PCT Filed: Oct. 18, 2017

(86) PCT No.: PCT/KR2017/011560
§ 371 (c)(1),
(2) Date: Dec. 11, 2017

(87) PCT Pub. No.: WO2018/074854
PCT Pub. Date: Apr. 26, 2018

(65) Prior Publication Data
US 2018/0325475 A1    Nov. 15, 2018

(30) Foreign Application Priority Data

Oct. 18, 2016 (KR) ........................ 10-2016-0134891
Dec. 16, 2016 (KR) ........................ 10-2016-0172677

(51) Int. Cl.
*A61B 6/14* (2006.01)
*H04N 5/232* (2006.01)
(Continued)

(52) U.S. Cl.
CPC ............... *A61B 6/14* (2013.01); *A61B 6/032* (2013.01); *A61B 6/463* (2013.01); *G06T 11/003* (2013.01);
(Continued)

(58) Field of Classification Search
None
See application file for complete search history.

(56) References Cited

U.S. PATENT DOCUMENTS 6,144,501 A    11/2000  Nalwa
7,039,156 B2 *  5/2006  Arai .................... A61B 6/0478
                                                                378/22
(Continued)

FOREIGN PATENT DOCUMENTS

JP    2001-333898 A    12/2001
JP    2004-313576 A    11/2004
(Continued)

OTHER PUBLICATIONS

European Patent Office, European Search Report of corresponding EP Patent Application No. 17807990.1, dated May 16, 2019.

*Primary Examiner* — Thomas R Artman
(74) *Attorney, Agent, or Firm* — IP Legal Services, LLC

(57) ABSTRACT

Disclosed is an X-ray image display apparatus with improved depth resolution, the display apparatus including a storage storing a plurality of X-ray frame data about a subject, an image processor reconstructing a first X-ray image by using a first group of X-ray frame data constituted by at least a portion of the plurality of X-ray frame data and reconstructing a second X-ray image by using a second group of X-ray frame data constituted by at least a portion of the plurality of X-ray frame data, a display configured to provide a screen, and a viewer module displaying a background image display part and a partial image display part disposed at a portion of the background image display part on the screen, displaying the first X-ray image on the background image display part, and displaying a portion of the second X-ray image corresponding to the first X-ray image on the partial image display part.

11 Claims, 19 Drawing Sheets

(51) Int. Cl.
*G06T 11/00* (2006.01)
*A61B 6/00* (2006.01)
*A61B 6/03* (2006.01)
*A61B 6/02* (2006.01)

(52) U.S. Cl.
CPC .......... *H04N 5/23238* (2013.01); *A61B 6/027* (2013.01); *A61B 6/467* (2013.01); *A61B 6/469* (2013.01); *A61B 6/5205* (2013.01); *A61B 6/5241* (2013.01); *A61B 6/54* (2013.01); *G06T 2207/10116* (2013.01); *G06T 2207/30036* (2013.01)

(56) References Cited

U.S. PATENT DOCUMENTS

| | | | |
|---|---|---|---|
| 8,254,520 B2 * | 8/2012 | Sadakane | A61B 6/032 378/19 |
| 8,433,033 B2 * | 4/2013 | Harata | A61B 6/583 378/38 |
| 8,634,515 B2 | 1/2014 | Cho et al. | |
| 8,861,679 B2 * | 10/2014 | Suuronen | A61B 6/00 378/98.5 |
| 10,492,742 B2 * | 12/2019 | Nakai | A61B 6/463 |
| 2004/0066877 A1 * | 4/2004 | Arai | A61B 6/0478 378/4 |
| 2004/0264753 A1 | 12/2004 | Capolunghi et al. | |
| 2006/0072848 A1 | 4/2006 | Razzano | |
| 2006/0203959 A1 | 9/2006 | Spartiotis et al. | |
| 2007/0064982 A1 | 3/2007 | Licato et al. | |
| 2008/0019477 A1 | 1/2008 | Spartiotis et al. | |
| 2008/0049894 A1 | 2/2008 | Yasuda et al. | |
| 2008/0063139 A1 | 3/2008 | Pantsar et al. | |
| 2009/0052617 A1 * | 2/2009 | Sadakane | A61B 6/032 378/38 |
| 2009/0232274 A1 | 9/2009 | Spartiotis et al. | |
| 2009/0232275 A1 | 9/2009 | Spartiotis et al. | |
| 2009/0310845 A1 | 12/2009 | Ogawa et al. | |
| 2010/0142673 A1 | 6/2010 | Pantsar et al. | |
| 2010/0177865 A1 | 7/2010 | Yoshimura | |
| 2010/0208866 A1 | 8/2010 | Spartiotis et al. | |
| 2010/0246761 A1 | 9/2010 | Pantsar et al. | |
| 2011/0044517 A1 | 2/2011 | Ro | |
| 2011/0305320 A1 * | 12/2011 | Suuronen | A61B 6/00 378/98.5 |
| 2012/0224762 A1 | 9/2012 | Choi et al. | |
| 2012/0230467 A1 | 9/2012 | Katsumata et al. | |
| 2012/0268556 A1 | 10/2012 | Cho et al. | |
| 2013/0003921 A1 | 1/2013 | Spartiotis et al. | |
| 2013/0108011 A1 | 5/2013 | Sadakane et al. | |
| 2013/0300822 A1 | 11/2013 | Mills | |
| 2013/0329854 A1 | 12/2013 | Spartiotis et al. | |
| 2014/0126686 A1 | 5/2014 | Sadakane et al. | |
| 2014/0254745 A1 * | 9/2014 | Nakai | A61B 6/466 378/4 |
| 2015/0117743 A1 | 4/2015 | Choi | |
| 2015/0139524 A1 | 5/2015 | Choi | |
| 2015/0146853 A1 | 5/2015 | Spartiotis et al. | |
| 2015/0305696 A1 | 10/2015 | Yamakawa et al. | |
| 2016/0015332 A1 | 1/2016 | Katsumata et al. | |
| 2016/0199014 A1 | 7/2016 | Choi et al. | |
| 2016/0310097 A1 | 10/2016 | Bae et al. | |
| 2017/0027536 A1 | 2/2017 | Choi | |
| 2017/0061651 A1 | 3/2017 | Choi | |
| 2017/0258420 A1 * | 9/2017 | Inglese | A61B 6/032 |
| 2017/0281101 A1 | 10/2017 | Choi et al. | |
| 2018/0108126 A1 * | 4/2018 | Choi | G06F 3/0481 |
| 2018/0108157 A1 * | 4/2018 | Choi | G06F 3/0481 |
| 2018/0325475 A1 * | 11/2018 | Choi | A61B 6/463 |

FOREIGN PATENT DOCUMENTS

| | | |
|---|---|---|
| JP | 2007-136163 A | 6/2007 |
| JP | 3983664 B2 | 9/2007 |
| JP | 2008-086659 A | 4/2008 |
| JP | 2009-531104 A | 9/2009 |
| JP | 2010-011910 A | 1/2010 |
| JP | 2013-116318 A | 6/2013 |
| JP | 2014-094092 A | 5/2014 |
| JP | 2014-514056 A | 6/2014 |
| JP | 2016-007338 A | 1/2016 |
| KR | 10-0917679 B1 | 9/2009 |
| KR | 10-2010-0120815 A | 11/2010 |
| KR | 10-1094180 B1 | 12/2011 |
| KR | 10-2012-0059498 A | 6/2012 |
| KR | 10-1389841 B1 | 4/2014 |
| KR | 10-1664166 B1 | 10/2016 |
| WO | 2012/135190 A2 | 10/2012 |
| WO | 2016/043562 A1 | 3/2016 |

* cited by examiner

X-RAY IMAGE DISPLAY APPARATUS AND METHOD FOR X-RAY IMAGE DISPLAY

CROSS REFERENCE TO RELATED APPLICATIONS

This application is a National Stage Patent Application of PCT International Patent Application No. PCT/KR2017/011560 (filed on Oct. 18, 2017) under 35 U.S.C. § 371, which claims priority to Korean Patent Application Nos. 10-2016-0134891 (filed on Oct. 18, 2016), and 10-2016-0172677 (filed on Dec. 16, 2016), the teachings of which are incorporated herein in their entireties by reference.

TECHNICAL FIELD

The present invention relates generally to an X-ray image display apparatus and a method for X-ray image display. More particularly, the present invention relates to an apparatus and a method for displaying first and second X-ray images on a screen by processing X-ray image data.

BACKGROUND ART

In the medical field, an X-ray apparatus refers to a device that transmits a predetermined amount of X-rays to a body part to be imaged, detects the transmitted X-rays with an X-ray sensor, and constructs an X-ray image based on detected electrical signals. The X-rays are attenuated and transmitted at different attenuation rates depending on the material on the traveling path, and when they reach the X-ray sensor, they are converted into electrical signals by photoelectric effect. The X-ray apparatus provides information about the inside of a subject as an X-ray image by using electrical signals with the cumulative amount of attenuation along the X-ray path being reflected in the image.

A computed tomographic (CT) image provides a three-dimensional X-ray image of the subject by reconstructing X-ray image data imaged at different angles while the X-ray generator that irradiates X-rays and the X-ray sensor that receives the X-rays are rotated around the subject.

A panoramic X-ray image is shown along an image layer as an arbitrary tomogram in the dental arch by superimposing a plurality of X-ray image data imaged by sections of the subject's dental arch through a so-called shift-and-add method, which is a tomography technique. The panoramic X-ray image is widely used particularly in the dental field.

The conventional panoramic X-ray image is problematic in that when a focusing area of the imaging apparatus, i.e., a reference image layer (predetermined image layer) determined by an imaging locus of the imaging apparatus is out of the actual dental arch locus of the subject, i.e., an interest area within the dental arch, the image of that part is not clear.

To solve the problem, there have been disclosed a technique for reconstructing a panoramic X-ray image of a plurality of image layers with a plurality of X-ray image data obtained through one imaging sequence (see Korean Patent No. 10-0917679), and a technique for providing a panoramic X-ray image that approximates the dental arch locus over the entire section of the panoramic X-ray image by choosing and combining the sharpest panoramic X-ray image that is closest to the dental arch locus through comparing panoramic X-ray images of a plurality of image layers by sections (see Korean Patent No. 10-1094180). There have been further disclosed a technique where after sizes of the images reconstructed along the image layers or sizes of the images used for reconstruction are scaled to be equal to the size of a reference image, all or a part of an image that clearly shows a predetermined interest area among the scaled images is selected, and the scaled images are divided into a plurality of blocks and the sharp images are selected from the divided block images, and a panoramic X-ray image is provided by using the selected images (see Korean Patent No. 10-1389841), and a technique where in the state where image data of a plurality of image layers is stored, a reference image layer is determined from a plurality of image layers, and a block corresponding to at least one block specified in the reference image layer is found in another image layer, after the clearest image is selected by comparing image data of the corresponding blocks, when the selected block is not the block specified in the reference image layer, the reference image layer is reconstructed and displayed by replacing the specified block of the reference image layer with the selected block of another image layer (see Korean Patent No. 10-1664166).

The panoramic X-ray image has the depth resolution, that is, the spatial resolution in the depth direction according to the X-ray irradiation direction, due to the characteristics of tomography technology. Here, the depth resolution of the panoramic X-ray image is inversely proportional to the depth of the image layer according to the X-ray irradiation direction, i.e., the thickness of the image layer. However, the conventional panoramic X-ray image is insufficient in the aspect of a depth resolution compared with computed tomography. For example, at the present level of panoramic X-ray image, it is difficult to distinguish the depth difference between the inner dental root and the outer dental root from a single image in one molar. Accordingly, some diseases such as periodontitis may not be found in panoramic X-ray images depending on where they occur.

A cephalometric X-ray image is a two-dimensional X-ray image of a head portion, which is divided into two methods: one-shot method for reconstructing a two-dimensional X-ray image of the imaging area with one directional X-ray image data transmitted through the entire imaging area; and scan method for reconstructing reconstructs a two-dimensional X-ray image of the imaging area with a plurality of X-ray image data obtained by scanning an X-ray passing through a part of the imaging area in the width direction. The cephalometric X-ray image is mainly used in the dental or ENT fields and is classified into LAT (lateral), AP (anteroposterior), PA (posteroanterior), SMV (submento vertex), and W/V (water's view) depending on the imaging direction.

However, since the cephalometric X-ray image is a two-dimensional X-ray image without depth resolution, that is, spatial resolution in the depth direction according to the X-ray irradiation direction, it is impossible to distinguish the desired, and as a result, to identify the section at a specific depth in a cephalometric X-ray image, computed tomography of the entire head must be performed, which causes unnecessary overexposure as well as economic burden on the subjects and hospitals.

DISCLOSURE

Technical Problem

Accordingly, the present invention has been made to overcome the limitation of conventional X-ray imaging technology in terms of depth resolution of an X-ray image and display efficiency of an X-ray image, and an object of the present invention is to provide an X-ray image display apparatus and a method for X-ray image display, in which it is possible to effectively provide an X-ray image of an image layer wherein the X-ray image has a quantity, thickness, angle, shape or position desired by a user by improving depth resolution and display efficiency of the X-ray image.

Technical Solution

In order to achieve the above object, according to some aspects of the present invention, there is provided an X-ray image display apparatus, including: a storage configured to store a plurality of X-ray frame data about a subject; an image processor configured to reconstruct a first X-ray image by using a first group of X-ray frame data constituted by at least a portion of the plurality of X-ray frame data, and to reconstruct a second X-ray image by using a second group of X-ray frame data constituted by at least a portion of the plurality of X-ray frame data; a display configured to provide a screen; and a viewer module configured to display a background image display part and a partial image display part disposed at a portion of the background image display part on the screen, to display the first X-ray image on the background image display part, and to display a portion of the second X-ray image corresponding to the first X-ray image on the partial image display part, wherein the first group of X-ray frame data and the second group of X-ray frame data are at least partially different from each other, and the second X-ray image is a tomographic X-ray image of at least one image layer.

According to some aspects of the present invention, there is further provided a method for displaying an X-ray image of an X-ray image display apparatus, in which the X-ray image display apparatus includes a storage, an image processor, a display, and a viewer module, the method including: storing a plurality of X-ray frame data of a subject in the storage; reconstructing a first X-ray image by using a first group of X-ray frame data constituted by at least a portion of the plurality of X-ray frame data by the image processor, and reconstructing a second X-ray image by using a second group of X-ray frame data constituted by at least a portion of the plurality of X-ray frame data by the image processor; and displaying a background image display part and a partial image display part disposed at a portion of the background image display part on a screen of the display by the viewer module, displaying the first X-ray image on the background image display part by the viewer module, and displaying a portion of the second X-ray image corresponding to the first X-ray image on the partial image display part by the viewer module, wherein the first group of X-ray frame data and the second group of X-ray frame data are at least partially different from each other, and the second X-ray image is a tomographic X-ray image of at least one image layer.

Advantageous Effects

According to the present invention configured as describe above, it is advantageous in that it is possible to effectively provide an X-ray image of an image layer wherein the X-ray image has a quantity, thickness, angle, shape or position desired by a user by improving depth resolution and display efficiency of the X-ray image. The apparatus according to the present invention is advantageous in that in the dental or ear-nose-and-throat (ENT) field, information about the image layers in different quantities, thicknesses, angles, shapes and locations in the dental arch or head can be provided in the form of a panoramic X-ray image or a cephalometric X-ray image.

MODE FOR INVENTION

Figure 1:
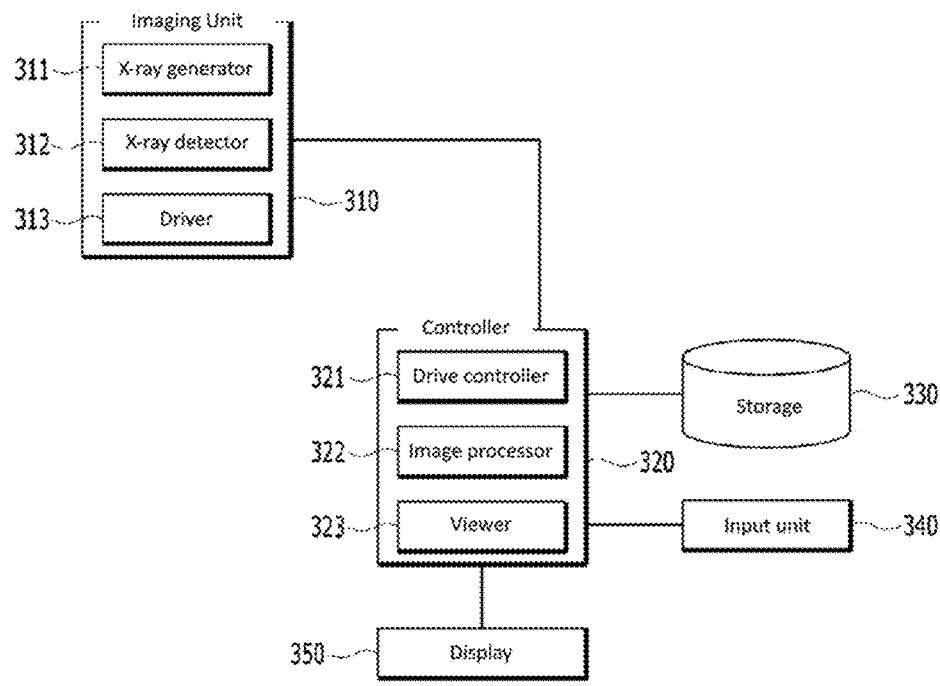
FIG. 1 shows a configuration of an X-ray image display apparatus according to the present invention.

Hereinafter, various embodiments of the present invention will be described with reference to the accompanying drawings. The technical idea of the present invention will be understood more clearly by the embodiments. The present invention is not limited to the embodiments described hereinbelow. The same reference numerals are used to designate the same or similar components, and a description of components having the same reference numerals as those described in any one of the drawings may be omitted.

FIG. 1 shows a configuration of an X-ray image display apparatus according to the present invention.

The X-ray image display apparatus according to the present invention includes: an imaging unit 310 having an X-ray generator 311 and an X-ray sensor 312; a controller 320 having an image processor 322 and a viewer module 323; a storage 330 configured to store X-ray image data and X-ray images of intermediate or final products obtained therefrom; an input unit 340 functioning as a user interface; and display 350 configured to display an X-ray image and various necessary images. The imaging unit 310 is provided with a driver 313 configured to move the X-ray generator 311 and the X-ray sensor 312 along a predetermined locus while facing each other, and the controller 320 is provided with a drive controller 321 configured to control the driver 313 and the X-ray generator 311, and operations of X-ray sensor 312. Meanwhile, the controller 320 includes a central processing unit, and may be configured to supervise all operations of the X-ray image display apparatus associated with the storage 330, the input unit 340, and the display 350 as well as the image processor 322 and the viewer module 323. The imaging unit 310 may be a separate device or may be wired or wirelessly connected to the controller 320.

The imaging unit 310 includes the X-ray generator 311 and the X-ray sensor 312, wherein the X-ray generator and the X-ray sensor are moved by the driver 313 while facing each other with a subject interposed therebetween. Here, the driver may move the X-ray generator 311 and the X-ray sensor 312 with the same facing each other about a rotation axis passing the X-ray generator 311 and the X-ray sensor 312 or passing between the X-ray generator 311 and the X-ray sensor 312, and the rotation axis may be moved one-dimensionally or two-dimensionally. When the scan sequence for obtaining an X-ray image is started, in parallel with the movement of the rotation axis, the X-ray generator 311 irradiates an imaging area with X-rays, and the X-ray sensor 312 obtains X-ray image data of a plurality of frames transmitted through the imaging area, that is, a plurality of X-ray frame data. The X-ray image data of a plurality of frames formed by X-ray beams irradiated at various positions and angles during the execution of a series of scan sequences reaching the X-ray sensor 312 will be referred to as a plurality of X-ray frame data, hereinbelow.

The controller 320 stores the plurality of X-ray frame data obtained from the imaging unit 310 in the storage 330, and the image processor 322 reconstructs first and second X-ray images by using the plurality of X-ray frame data. The viewer module 323 displays the reconstructed first and second X-ray images on a screen. Herein, the reconstructed first and second X-ray images may be stored again in the storage 330.

Not shown in the drawings, in the X-ray image display apparatus according to the present invention, the controller 320, the storage 330, the input unit 340, and the display 350 may be implemented in the form of one or more computer devices and their peripheral devices.

The input unit 340 may be a mouse. Other than this, the input unit 340 may include a keyboard of a computer, a keypad, a touchpad, and the like, and the type of the input means is not limited thereto. For example, the input unit 340 is controllable using the illustrated input means, and may include a graphic user interface displayed on the display 350 through the controller 320.

As described, the controller 320 includes the central processing unit (CPU) generally controlling operations of the X-ray image display apparatus according to the present invention. As an example, the controller 320 may be implemented using at least one of application specific integrated circuits (ASICs), digital signal processors (DSPs), digital signal processing devices (DSPDs), programmable logic devices (PLDs), field-programmable gate arrays (FPGAs), processors, controllers, micro-controllers, and microprocessors. The controller 320 may also be implemented as a firmware/software module that is executable on the above hardware platform. In this case, the firmware/software module may be implemented by one or more software applications in an appropriate program language.

The viewer module 323 displays the first and second X-ray images reconstructed in the image processor 322 on the screen. Here, the viewer module 323 may be implemented as a firmware/software module having a series of functions for displaying the viewer module screen in a predetermined format on the display 350 according to the pre-stored algorithm and appropriately displaying the first and second X-ray images reconstructed in the image processor 322 according to the user's input to the input unit 340, and providing an additional function required by the user. The viewer module 323 may be included as part of the image processor 322.

The storage 330, which is a digital data storage medium, stores data related to setting various image and parameter values for performing operations of the X-ray image display apparatus as well as X-ray frame data obtained from the X-ray sensor 312, X-ray image data generated in image processing or reconstructed as a result of image processing, the first and second X-ray images, and the like. As an example, the storage 330 may include a flash memory type storage medium such as a solid state disk (SSD), a memory card, or a memory stick, or may be a disk type storage medium such as a hard disk, an optical disk, or the like. Some or all of the storage 330 may be located remotely from the controller 320, or may be distributed at various locations. It will be appreciated by those skilled in the art that implementations of storage media are not limited to the examples described above.

The display 350 is an image display device capable of outputting a viewer module screen configured in a predetermined format and an X-ray image. The display 350 may include various display devices such as an LCD display, an LED display, an AMOLED display, and a CRT display, and may be a touch display panel, in which case the input unit 340 described above may include a touch interface.

The X-ray image display apparatus according to the present invention configured as described above displays the first and second X-ray images that are visually different through the screen of the display 350, and particularly, displays the first X-ray image on a background image display part that is a predetermined area in the screen and displays the second X-ray image corresponding to a portion of the first X-ray image on a partial image display part disposed at a portion of the background image display part.

Here, preferably, the first and second X-ray images may be respectively reconstructed in the image processor 322 by using at least a portion of the X-ray frame data obtained through a single scan sequence of the imaging unit 310. Particularly, the first X-ray image may be a tomographic X-ray image of at least one image layer, which is an arbitrary tomogram in the imaging area, or a two-dimensional X-ray image, and the second X-ray image may be a tomographic X-ray image of at least one image layer in the imaging area.

Further, preferably, by the viewer module 323, at least one of size, position, shape, and quantity of the partial image display part, and at least one of quantity, position, shape, angle, and thickness of an image layer of the second X-ray image may be changed according to the user's choice, and the second X-ray image for each image layer may be reconstructed in advance and stored in the storage 330.

Meanwhile, in the X-ray image display apparatus according to the present invention, the first X-ray image may be a tomographic X-ray image or a two-dimensional X-ray image, and the second X-ray image may be a tomographic X-ray image. Particularly, when the first X-ray image is a tomographic X-ray image, it is suitable for seeing a subject's dental arch structure through the X-ray image display apparatus according to the present invention, that is, it is suitable for panoramic X-ray image diagnosis, and when the second X-ray image is a two-dimensional X-ray image, it is suitable for seeing a subject's head structure through the X-ray image display apparatus according to the present invention, that is, it is suitable for cephalometric X-ray image diagnosis.

In other words, when the first X-ray image is a panoramic X-ray image, the X-ray image display apparatus according to the present invention provides a second panoramic X-ray image of at least one second image layer, which is at least partially different or completely different from the first image layer for a predetermined portion of the first panoramic X-ray image, as the second X-ray image, along with a first panoramic X-ray image of at least one first image layer as the first X-ray image. Here, preferably, it is possible to considerably improve the depth resolution of the first and/or the second panoramic X-ray images compared to a conventional panoramic X-ray image, and it is possible to increase display efficiency by providing a screen configuration different from the conventional one so that the first and second panoramic X-ray images can be effectively used for dental treatment.

Further, when the first X-ray image is a cephalometric X-ray image, the X-ray image display apparatus according to the present invention provides a tomographic X-ray image of at least one image layer for a predetermined portion of the two-dimensional X-ray image as the second X-ray image, along with a two-dimensional X-ray image of the head as the first X-ray image. Here, preferably, it is possible to considerably improve the depth resolution of a tomographic X-ray image compared to a conventional tomographic X-ray image, and it is possible to increase display efficiency by proving a screen configuration different from the conventional one so that the two-dimensional X-ray image and the tomographic X-ray image can be effectively used for dental or ENT treatment.

Hereinbelow, the technical features of the present invention will be described in more detail with reference to the configuration shown in FIG. 1. For convenience, when the first X-ray image is a tomographic X-ray image, the first and second X-ray images are referred to as first and second panoramic X-ray images, and when the first X-ray image is a two-dimensional X-ray image, the first and second X-ray images are referred to as a cephalometric image and a tomographic X-ray image, respectively. The technical idea of the present invention will be described in detail through the former, and the latter will be mainly discussed with respect to the difference.

Figure 2:
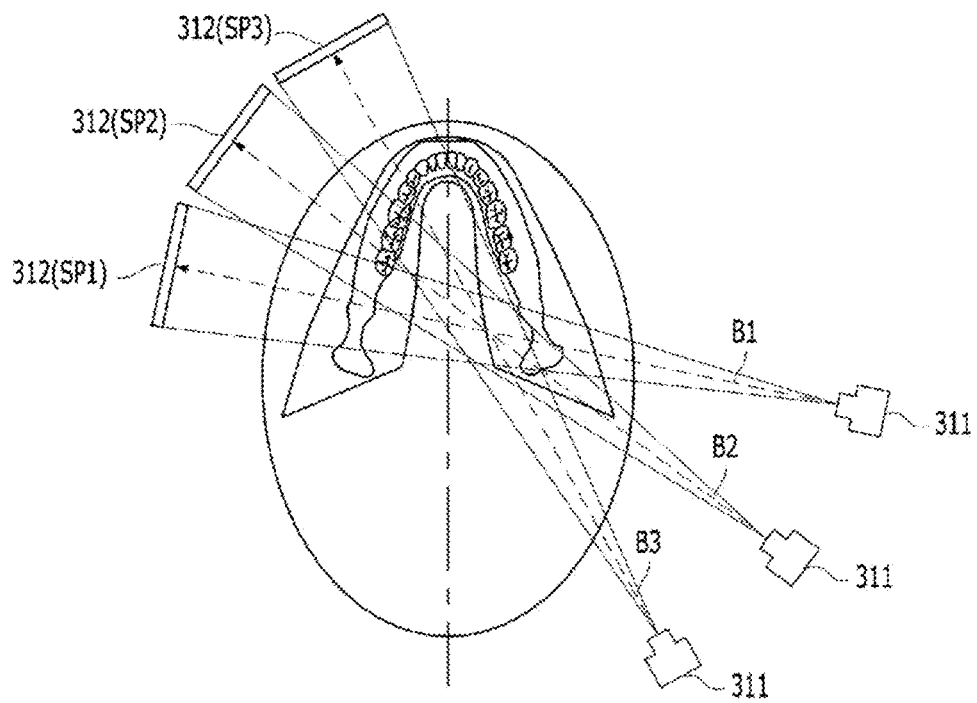
FIG. 2 roughly shows a state where a scan sequence of the X-ray image display apparatus according to an embodiment of the present invention is performed.

FIG. 2 roughly shows a state where a scan sequence of the X-ray image display apparatus according to an embodiment of the present invention is performed.

As shown in the drawings, the X-ray generator 311 and the X-ray sensor 312 are rotated while facing each other with the subject's dental arch interposed therebetween. In this process, the X-ray sensor 312 receives X-ray beams (B1, B2, B3, . . . ) transmitted from various angles at various positions in the dental arch, and generates X-ray frame data containing an X-ray receiving signal of one frame for each of the positions (SP1, SP2, SP3, . . . ). In this manner, a single scan sequence is performed.

Herein, the scan sequence is a series of processes in which a plurality of X-ray image data, which are a plurality of X-ray image data obtained from the X-ray sensor 312 on a frame-by-frame basis, are obtained while the imaging unit 310 continuously moves along a predetermined locus. A technique for acquiring X-ray frame data necessary for reconstructing a panoramic X-ray image of a plurality of different image layers through a single scan sequence is disclosed in the document of Korean Patent No. 10-0917679 of the applicant's prior patent.

Herein, a single scan sequence may be constituted by a motion of the imaging unit 310 that is the same as or similar to the conventional panoramic X-ray imaging operation. However, in this case, the width (width toward the moving direction) of the X-ray sensor 312 is preferably wider than the width of the X-ray sensor of the conventional panoramic X-ray imaging apparatus. For example, compared to the X-ray sensor of the conventional panoramic X-ray imaging apparatus having a width of 6 mm, the apparatus according to the present invention employs the X-ray sensor 312 having a width of about 4 to 6 cm, whereby it is also possible to obtain sufficient data to increase the depth resolution through the same imaging locus. Further, the single scan sequence may be constituted by a motion of the imaging unit that is the same as or similar to the motion of a conventional CT imaging operation, and it will be understood by those skilled in the art that various changes and modifications may be made without being limited to the mentioned example.

Figure 3:
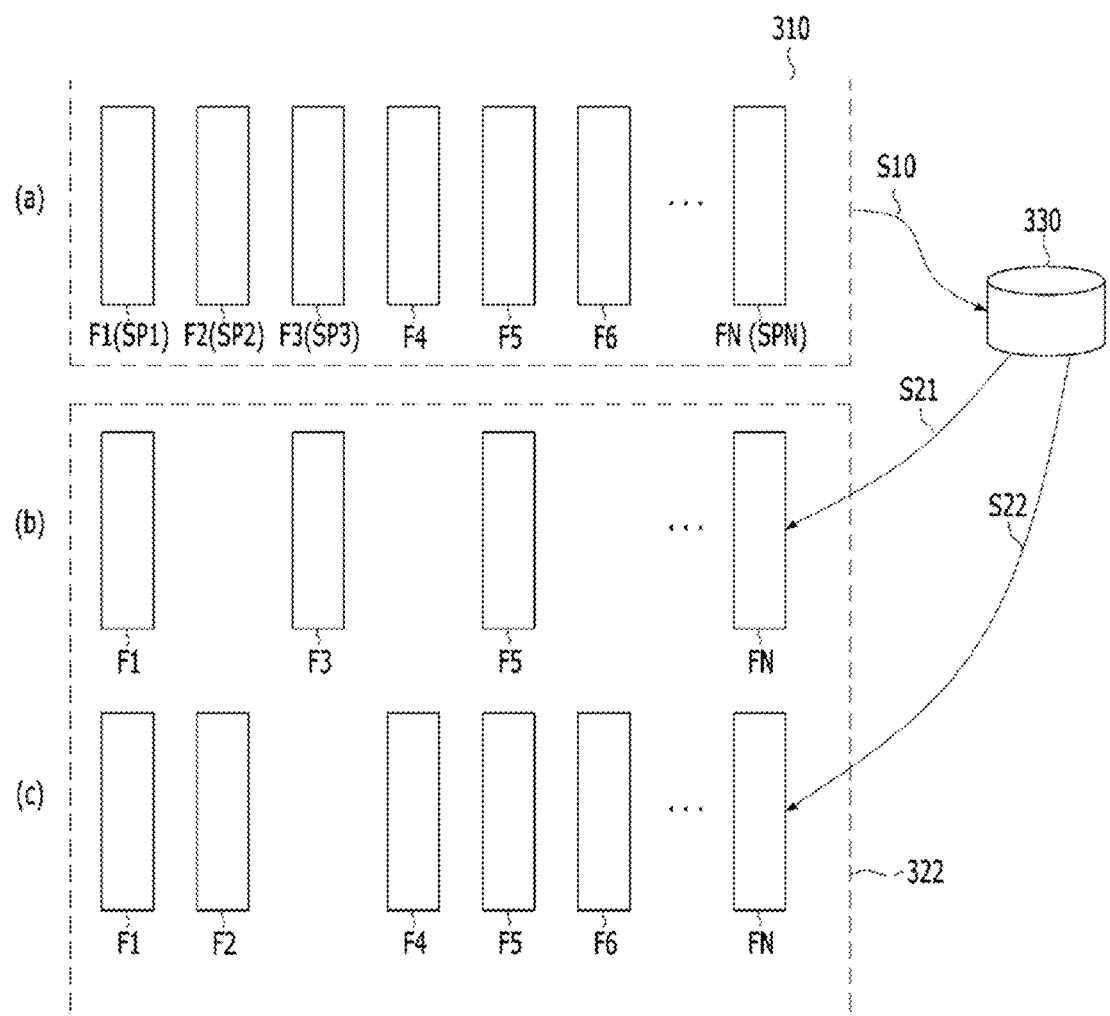
FIG. 3 schematically shows a process of obtaining a plurality of X-ray frame data according to performance of the scan sequence of FIG. 2 and reconstructing a panoramic X-ray image using the X-ray frame data.

FIG. 3 schematically shows a process of obtaining a plurality of X-ray frame data according to performance of the scan sequence of FIG. 2 and reconstructing a panoramic X-ray image using the X-ray frame data.

FIG. 3a shows a plurality of X-ray frame data (F1, F2, F3, F4, F5, F5, ~, FN) obtained through a single scan sequence of the imaging unit 310 (S10). The plurality of X-ray frame data (F1, ~, FN) are constituted by X-ray image data of a plurality of frames generated by receiving X-ray beams respectively transmitted through a portion of the dental arch as the imaging area at various angles through the X-ray sensor 312 while the imaging unit 310 performs a single scan sequence, such as a first X-ray frame data F1 generated as a result of the X-ray sensor 312 (see FIG. 2) receiving a first X-ray beam B1 at SP1 position, a second X-ray frame data F2 generated as a result of the X-ray sensor receiving a second X-ray beam B2 at SP2 position, a third X-ray frame data F3 generated as a result of the X-ray sensor receiving a third X-ray beam B3 at SP3 position, and the like. The plurality of X-ray frame data (F1, ~, FN) are stored in the storage 330. Here, each of the X-ray frame data (F1, ~, FN) may be stored together with information about the location and direction of the X-ray beam transmitted through the imaging area.

FIGS. 3b and 3c schematically show that the image processor 322 extracts a necessary plurality of X-ray frame data from the storage 330 to reconstruct the first and second panoramic X-ray images, respectively. To be more specific, FIG. 3b shows a first group of X-ray frame data (F1, F3, F5, . . . , FN) extracted from the population of the plurality of X-ray frame data in order to reconstruct the first panoramic X-ray image (S21). FIG. 3c shows a second group of X-ray frame data (F1, F2, F4, F5, F6, . . . , FN) extracted from the population of the plurality of X-ray frame data in order to reconstruct the second panoramic X-ray image different from the first panoramic X-ray image (S22). In the drawings, numerals of selected frames in each of the first group of X-ray frame data listed in FIG. 3b and the second group of X-ray frame data listed in FIG. 3c are arbitrarily selected and have no special meaning.

However, of the plurality of X-ray frame data, the first group of X-ray frame data and the second group of X-ray frame data satisfy the following conditions. The first group of X-ray frame data and the second group of X-ray frame data may be partially overlapped but not identical, and the number of frames of the first group of X-ray frame data and the number of frames of the second group of X-ray frame data may be the same or different from each other. Here, the composition and the number of the first group of X-ray frame data and the second group of X-ray frame data may be appropriately adjusted according to the purpose. As an example, when the depth resolution of the first panoramic X-ray image is lower than that of the second panoramic X-ray image, that is, when the thickness of the second image layer, which is the focusing area of the second panoramic X-ray image, is thinner than that of the first image layer, which is the focusing area of the first panoramic X-ray image, the number of frames of the X-ray frame data constituting the first group may be smaller than that of the X-ray frame data constituting the second group. To improve depth resolution, a larger number of X-ray frame data obtained in a wider angle range for each part of the imaging area, which is the dental arch, is required.

Herein, of the population of the plurality of X-ray frame data stored in the storage 330, in order to reconstruct the first panoramic X-ray image (s21) or the second panoramic X-ray image (s22), whether to extract the X-ray frame data selectively and constitute the first group and the second group depends on the characteristics of the first and second image layers, which are the focusing areas of the respective panoramic X-ray images. Reference will be made in detail to the first and second image layers, hereinafter.

Figure 4:
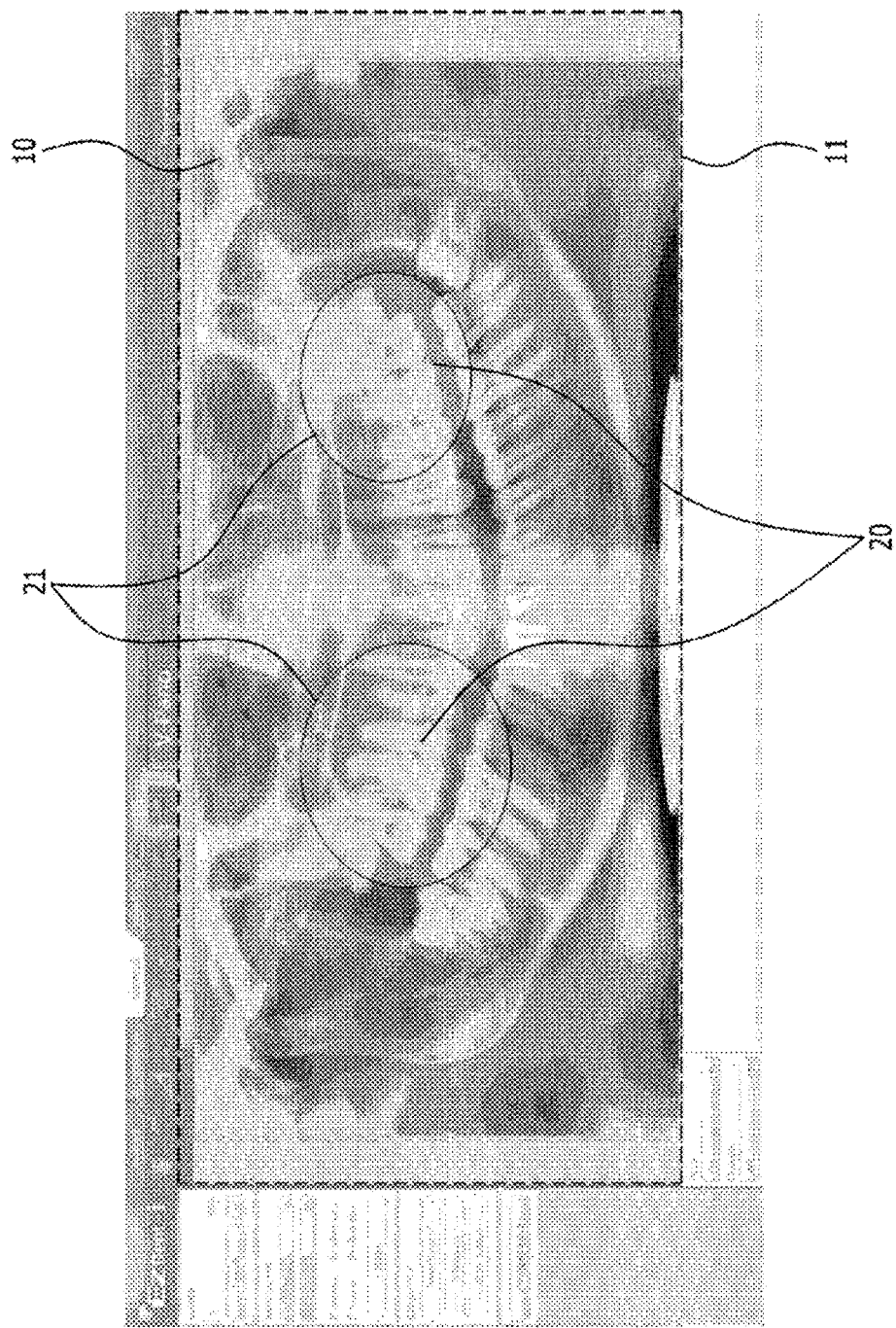
FIG. 4 shows an example of a display screen of the X-ray image display apparatus according to the present invention.

FIG. 4 shows an example of a display screen of the X-ray image display apparatus according to the present invention.

The screen output through the X-ray image display apparatus according to the present invention is provided with the background image display part 11 displaying the first panoramic X-ray image 10, which is the panoramic X-ray image of at least one first image layer, and is also provided with the partial image display part 21 disposed at a predetermined portion of the background image display part 11 and configured to display a portion of the second panoramic X-ray image 20 as the panoramic X-ray image of at least one second image layer corresponding to the predetermined portion, which is at least partially different or completely different from the first image layer.

The partial image display part 21 may be provided one or more in number. Further, according to the user's input, for example, through a mouse input, the size, position, shape or quantity of the partial image display part 21 may be adjusted. However, since the partial image display part 21 is provided for enhancing the efficiency of diagnosis by reinforcing the depth resolution of the first panoramic X-ray image 10, it is desirable to include a portion of the subject's teeth that needs confirmation of various depths. For example, in the case of a maxillary dental arch, it is preferable to include a maxillary molar in which a dental root is disposed at the outer side and the inner side of the tooth that needs confirmation.

Meanwhile, the partial image display part 21 may be configured such that a user (e.g., a dentist) first checks the first panoramic X-ray image 10 provided through the background image display part 11, and when it is necessary to further review a predetermined part, the predetermined part is selectively activated according to the user's instructions, and the corresponding second panoramic X-ray image 20 of the second image layer is displayed by superimposing on the first panoramic X-ray image of that part or by replacing first panoramic X-ray image of that part. The second panoramic X-ray image 20 may be displayed with a different brightness or color than the first panoramic X-ray image 10. Further, the border between the first panoramic X-ray image 10 and the second panoramic X-ray image 20 may be displayed by displaying the edge of the partial image display part 21 on the screen.

To achieve this, the image processor reconstructs the first panoramic X-ray image of at least one first image layer by using a plurality of frames of X-ray image data obtained through a single scan sequence performed by the imaging unit, and also reconstructs the second panoramic X-ray image 20 of at least one second image layer, which is at least partially different or completely different from the first image layer, and provides the same to the viewer module. To achieve this, the image processor may store the first and second panoramic X-ray images of the first and second image layers by reconstructing the same in advance. Herein, the scan sequence referred to as a series of processes in which a plurality of X-ray image data is obtained at different angles while the imaging unit continuously moves along a predetermined locus.

A single scan sequence may be constituted by a motion of the imaging unit 310 that is the same as or similar to the conventional panoramic X-ray imaging operation, or may be different from the conventional panoramic X-ray imaging operation. Further, the single scan sequence may be constituted by a motion of the imaging unit that is the same as or similar to a conventional CT scanner, or may be different from the conventional CT scanner. In other words, the motion of the imaging unit during the single scan sequence may vary as long as a plurality of X-ray image data radiographed from different angles with respect to the dental arch is obtained, so that the first and second panoramic X-ray images can be reconstructed.

However, in this case, the width (width toward the moving direction) of the X-ray sensor is preferably wider than the width of the X-ray sensor of the conventional panoramic X-ray imaging apparatus. For example, compared to the X-ray sensor of the conventional panoramic X-ray imaging apparatus having a width of 6 mm, the apparatus according to the present invention employs the X-ray sensor, whose width is more than that of a general X-ray sensor, preferably, is 10 mm or more, whereby it is possible to obtain X-ray image data with a sufficient angle range to increase the depth resolution of the first and second panoramic X-ray image. For reference, in the panoramic X-ray imaging apparatus, since the height of the X-ray sensor can vary depending on the desired panoramic imaging area or the size of the panoramic X-ray image, it is difficult to specify a specific range, but it is generally between 100 mm and 200 mm. In the present invention the width of the X-ray sensor can also be adjusted according to the scan sequence of the imaging, and particularly, assuming a scan sequence similar to a typical panoramic X-ray imaging apparatus, in order to obtain X-ray image data of a larger angle range, the width of the X-ray sensor is 10 mm or more, and preferably, 18 mm or more, which is larger than the width of a general X-ray sensor.

Specific details for improving the depth resolution of the first and second panoramic X-ray images will be described in detail with reference to FIG. 10 and the related description.

Meanwhile, the first panoramic X-ray image is a panoramic X-ray image of at least one first image layer, may be a panoramic X-ray image of an image layer or a panoramic X-ray image in which panoramic X-ray images of two or more image layers are superimposed.

Further, the second panoramic X-ray image is a panoramic X-ray image of at least one second image layer, which is at least partially different or completely different from the first image layer, wherein when the first panoramic X-ray image is a panoramic X-ray image of an image layer, the second panoramic X-ray image may be a panoramic X-ray image of another image layer different from the first image layer of the first panoramic X-ray image, a panoramic X-ray image in which the first image layer of the first panoramic X-ray image and a panoramic X-ray image of at least one image layer different from the first image layer are superimposed, or a panoramic X-ray image in which panoramic X-ray images of two or more image layers different from the first image layer of the first panoramic X-ray image are superimposed. When the first panoramic X-ray image is the superimposed panoramic X-ray image of two or more image layers different from each other, the second panoramic X-ray image may be a panoramic X-ray image of a image layer of the first image layers of the first panoramic X-ray image, a panoramic X-ray image of an image layer different from the first image layers of the first panoramic X-ray image, a panoramic X-ray image in which panoramic X-ray images of at least one of the first image layers of the first panoramic X-ray image and at least one image layer different therefrom are superimposed, or a panoramic X-ray image in which panoramic X-ray images of two or more image layers different from the first image layers of the first panoramic X-ray image are superimposed.

Here, preferably, the first panoramic X-ray image is configured such that the panoramic X-ray images of a plurality of first image layers are superimposed so as to display wider information along the X-ray irradiation direction, and the second panoramic X-ray image may be a panoramic X-ray image of the second image layer corresponding to any one of the first image layers so as to enhance the depth resolution of the first panoramic X-ray image.

Herein, a panoramic X-ray image for each image layer may be a panoramic X-ray image of the same magnification that expresses the same zooming in the same range in the same plane, and superimposition may mean to display a single panoramic X-ray image in which all the panoramic X-ray images for each image layer are substantially reflected by adding, averaging, or taking the representative value of the pixel values of the panoramic X-ray image for each image layer along the X-ray irradiation direction.

In other words, it is sufficient that the first and second panoramic X-ray images are panoramic X-ray images having different depth resolutions through selection and combination of panoramic X-ray images for a plurality of image layers, and they may be freely selected according to the user's purpose. Further, the first and second image layers for the first and second panoramic X-ray images may be adjusted in quantity, position, shape, angle, and thickness thereof according to the user's purpose, while will be described through examples. For convenience, the first and second image layers will be described as being different from each other.

Meanwhile, the image layer of the panoramic X-ray image includes a focal curved surface that is the basis for focusing when the panoramic X-ray image is reconstructed. Accordingly, in a panoramic X-ray image of an arbitrary image layer, not only a structure on the focal curved surface but also a structure existing within the front and back predetermined regions of the focal curved surface is projected with respect to the X-ray irradiation direction. However, according to the thickness of image layer, the structure on the focal curved surface and the structure existing within the predetermined regions of the focal curved surface are different in sharpness, wherein the relative difference is expressed as the thickness of the image layer. In other words, the relatively thin thickness of the image layer means that the front and back regions of the focal curved surface, which are clearly projected on the panoramic X-ray image based on the focal curved surface, are relatively narrow with respect to the X-ray irradiation direction, which means that the depth resolution of panoramic X-ray image is high. However, in the drawings described below, the thickness of the image layer is relatively expressed, and the thickness shown in the drawings does not indicate its absolute thickness.

Meanwhile, preferably, the thickness of the second image layer may be thinner than that of the first image layer. In other words, it is preferred that the depth resolution of the second panoramic X-ray image be better than that of the first panoramic X-ray image. To achieve this, the image processor according to the present invention may use X-ray image data with a wider angle range penetrating each point of the second image layer when reconstructing the second panoramic X-ray image.

Instead, the thicknesses of the first and second image layers may be the same, which is thinner than that of the image layer of a general panoramic X-ray image, and the depth resolutions of the first and second panoramic X-ray images may be higher than that of the general panoramic X-ray image. The details of increasing the depth resolution of the first and/or second panoramic X-ray image by adjusting the thicknesses of the first and/or second image layers will be described in detail with reference to FIG. 10 and the related description.

Figure 5:
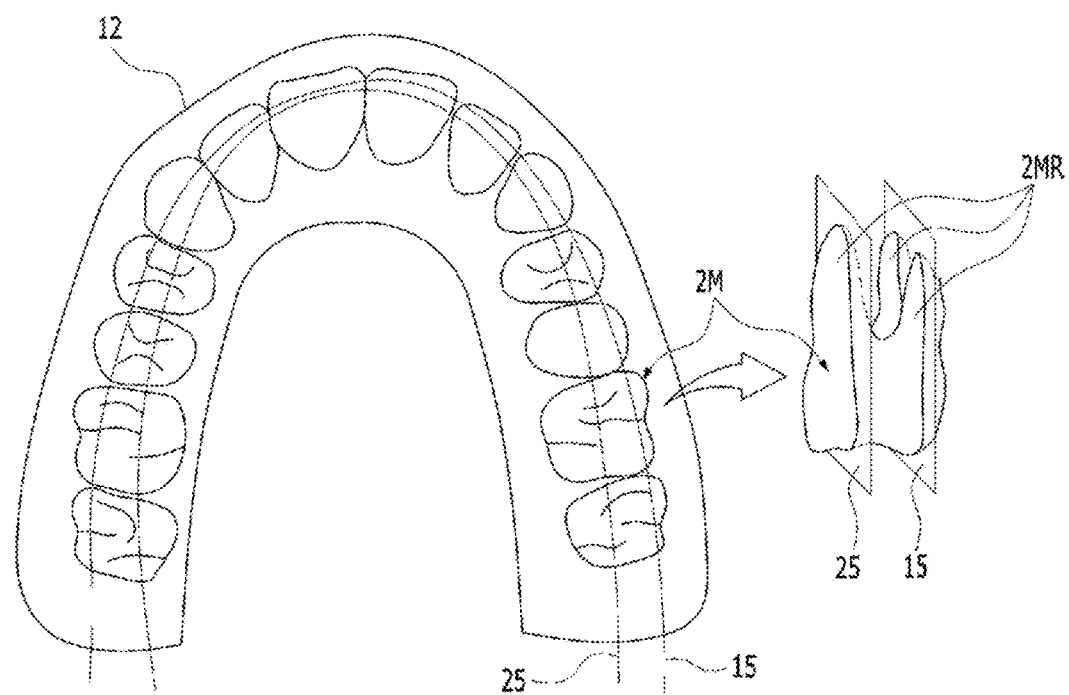
FIG. 5 shows an example of first and second image layers of first and second panoramic X-ray images displayed on the display screen according to the embodiment of FIG. 4.

FIG. 5 shows an example of first and second image layers of first and second panoramic X-ray images displayed on the display screen according to the embodiment of FIG. 4.

This figure shows an example of a first image layer 15 and a second image layer 25 described above indicated in the shape of a maxillary dental arch 12, which is a part of the interest area of the panoramic X-ray image. A panoramic X-ray image of the first image layer 15 may be the first panoramic X-ray image 10 of FIG. 1, and a panoramic X-ray image of the second image layer 25 may be the second panoramic X-ray image 20. However, herein, quantity, position, shape, angle, and the like of the first and second image layers 15 and 25 are just examples, and may be different from the image layer of the panoramic X-ray image shown in FIG. 4.

In the embodiment, the second image layer 25 and the first image layer 15 are different from each other in at least one of quantity, position, shape, and angle. Herein, the shape refers to the overall shape of the curvature of the various parts forming the image layer.

Meanwhile, on the right side of this figure, the shape of the second maxillary molar 2M and the first and second image layers 15 and 25 passing through the second maxillary molar are three-dimensionally enlarged. In the case of the second maxillary molar 2M, there are two dental roots 2MR on the outer side of the arch, that is, near the lip, and one dental root 2MR on the inner side of the arch, that is, near the tongue. Accordingly, two dental roots 2MR are shown in the first panoramic X-ray image reconstructed by focusing the first image layer 15, but one dental root 2MR is shown in the second panoramic X-ray image reconstructed by focusing the second image layer 25. As described above, the second panoramic X-ray image of the second image layer 25 provides panoramic X-ray image information about image layer with quantity, position, shape, and angle different from the first panoramic X-ray image.

Further, herein, one first image layer 15 and one second image layer 25 different from the first image layer are shown, but the first and/or the second image layer 25 may be a plurality of image layers different from each other in at least one of quantity, position, shape, and angle, wherein the first and second image layers 15 and 25, particularly, quantity, position, shape, and angle of the second image layer 25 may be variously changed according to the user's choice. For reference, the user's choice may be input into the viewer module via the input unit, and the viewer module may display the second panoramic X-ray image according to the user's choice by displaying the control menu on the screen to allow the user's choice to be input.

Figure 6:
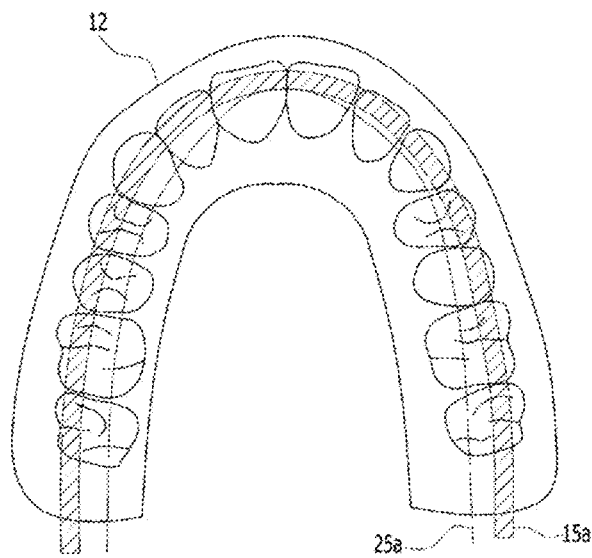
FIG. 6 shows another example of the first and second image layers of the first and second panoramic X-ray images displayed on the display screen according to the embodiment of FIG. 4.

FIG. 6 shows another example of the first and second image layers of the first and second panoramic X-ray images displayed on the display screen according to the embodiment of FIG. 4.

As in the embodiment, the thickness of a first image layer 15*a* may be thicker than that of a second image layer 25*a*. This means that the information about the internal structure of a relatively thicker image layer, that is, relatively large area with respect to the X-ray irradiation direction is two-dimensionally superimposed on the first panoramic X-ray image. As described above, the first image layer 15*a* and the second image layer 25*a* may be different in thickness as well as in quantity, position, shape, and angle. The second image layer 25*a* may be partially or fully superimposed on the first image layer 15*a*, or may be totally different from the first image layer 15*a*.

Further, one first image layer 15*a* and one second image layer 25*a* different from the first image layer are shown, but the first and/or the second image layer 25*a* may be a plurality of image layers different from each other in at least one of quantity, position, shape, and angle, wherein the first and second image layers 15*a* and 25*a*, particularly, quantity, position, shape, and angle of the second image layer 25 may be variously changed according to the user's choice.

Figure 7:
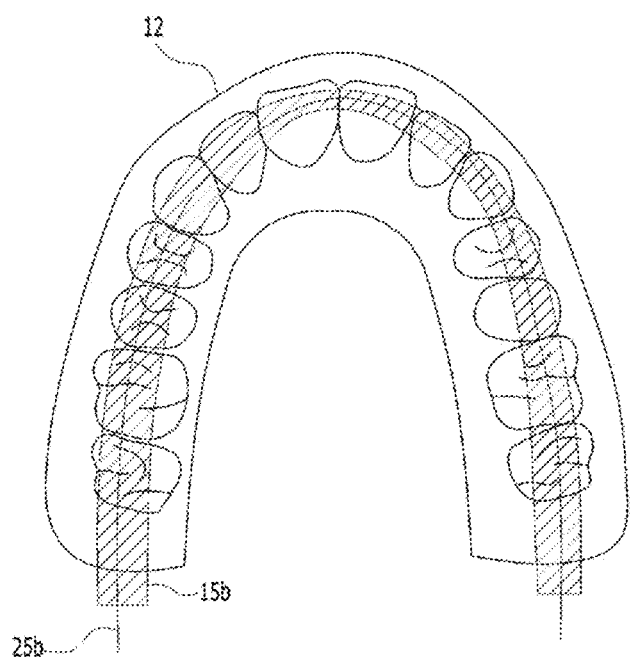
FIG. 7 shows a further example of the first and second image layers of the first and second panoramic X-ray images displayed on the display screen according to the embodiment of FIG. 4.

FIG. 7 shows a further example of the first and second image layers of the first and second panoramic X-ray images displayed on the display screen according to the embodiment of FIG. 4.

As in the embodiment, a first image layer 15*b* and a second image layer 25*b* are generally superimposed on each other, wherein the thickness of the first image layer 15*b* may be thicker than that of the second image layer 25*b*. For example, the first image layer 15*b* of the first panoramic X-ray image may be set to have a thickness thicker than that of the second image layer, for example, a thickness including almost thicknesses of teeth arranged along a locus of the dental arch, and the second image layer 25*b* of the second panoramic X-ray image has a thinner thickness within the first image layer, whereby it is possible to provide the second panoramic X-ray image sharper than the first panoramic X-ray image, that is, it is possible to provide a panoramic X-ray image with improved depth resolution.

Meanwhile, in the embodiment of FIGS. 6 and 7, the first panoramic X-ray image may be a panoramic X-ray image of one thick image layer or may be a shape of a panoramic X-ray image of one image layer with a substantially thick thickness by superimposing panoramic X-ray images of a plurality of image layers each having a thin thickness. In this case, the second panoramic X-ray image may be one of a plurality of panoramic X-ray images superimposed to reconstruct the first panoramic X-ray image. Here, a panoramic X-ray image for each image layer may show the same magnification, and as a result, the first and second panoramic X-ray images show the same magnification.

Meanwhile, it is described that a single panoramic X-ray image can be realized by superimposing panoramic X-ray images of a plurality of image layers. Alternatively, the X-ray image processor according to the present invention may provide a panoramic X-ray image of a relatively thicker image layer than the existing panoramic X-ray image. In other words, the X-ray image processor according to the present invention is capable of freely adjusting the thickness of an image layer of a panoramic X-ray image, whereby it is possible to freely adjust the depth resolution of a panoramic X-ray image.

The details of adjusting the depth resolution of a panoramic X-ray image by adjusting the thickness of an image layer will be described in detail with reference to FIG. 10 and the related description.

Preferably, in setting the shape and position of the second image layer 25*b*, by allowing the second image layer 25*b* to include a portion where tomography is performed at the time of dental treatment, the speed and convenience of the treatment can be enhanced and the X-ray dose of the subject can be greatly reduced. Meanwhile, also in this case, the number of the first and/or second image layers 15*b* and 25*b* is not limited to one, and the first and second image layers 15*b* and 25*b*, particularly, the second image layer 25*b* may be variously changed according to the user's choice.

Figure 8:
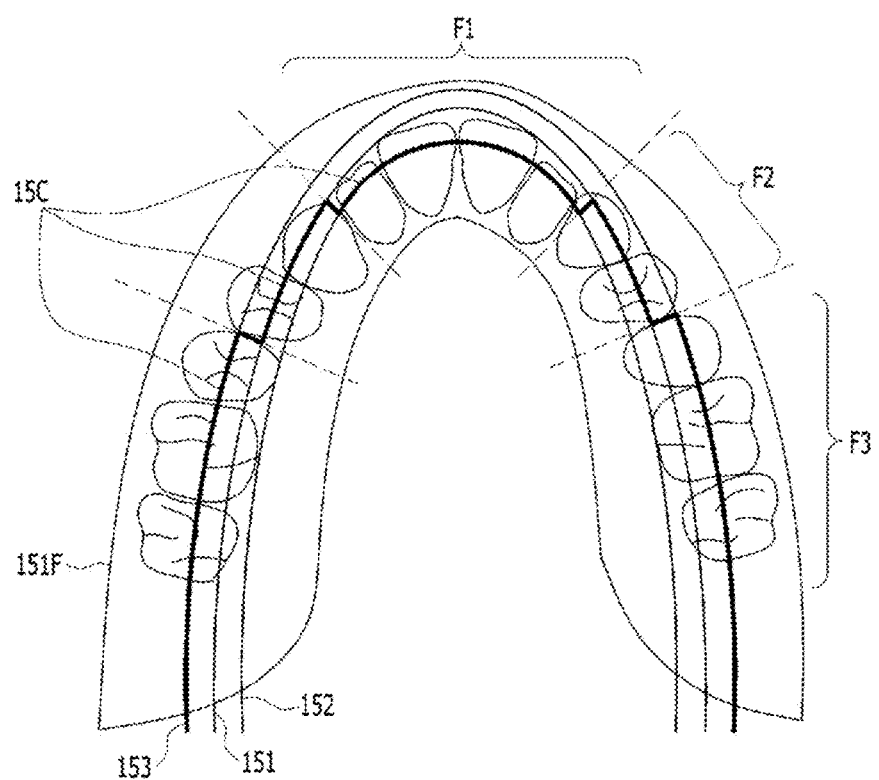
FIG. 8 shows an example of the first image layer of the first panoramic X-ray image displayed on the display screen according to the embodiment of FIG. 4.

FIG. 8 shows an example of the first image layer of the first panoramic X-ray image displayed on the display screen according to the embodiment of FIG. 4.

The first panoramic X-ray image may be a panoramic X-ray image that is auto-focused over the entire sections by dividing a plurality of image layers, i.e., the multi-image layer, into the same sections and selecting image layers of the sharpest section for each section and connecting the same. In this case, as shown in the drawing, the first image layer may be connected discontinuously or continuously with different positions by a plurality of sections divided along the longitudinal direction of the dental arch.

Looking more closely at these examples, first, an arbitrary image layer 151 is shown in the drawing. The arbitrary image layer may be a predetermined image layer determined by the imaging locus of the apparatus. Reference numeral 151F designates an imaging area 151F of a panoramic X-ray image. The X-ray image display apparatus according the embodiment of the present invention reconstructs a panoramic X-ray image for an inner image layer 152 disposed at the inside of the arbitrary image layer 151 in the imaging area, and also reconstructs a panoramic X-ray image for an outer image layer 153 disposed at the outside of the arbitrary image layer 151 in the imaging area.

Here, the panoramic X-ray image for the arbitrary image layer and the panoramic X-ray images for the inner and outer image layers may be separately, that is, may be reconstructed based on different X-ray image data, or the panoramic X-ray images for the inner and outer image layers may be reconstructed by using the X-ray image data of the panoramic X-ray image for the arbitrary image layer. A specific method for the latter can be referred to in the document of Korean Patent No. 10-0917679 by the applicant of the present invention, and a specific method of the former can be referred to in FIG. 10 and the related description.

Of the reconstructed panoramic X-ray images for a plurality of image layers, the sharpest image layer, which is the closest to the dental arch locus of the actual subject, is selected for each section, and by reconstructing a panoramic X-ray image of the final image layer, in which the selected image layers are connected to each other, the first panoramic X-ray image, in which a plurality of different panoramic X-ray images, are connected by horizontal sections, can be completed. In this case, assuming that a final image layer corresponding to the first panoramic X-ray image is a first image layer 15c, the first image layer 15c is, for example, a shape in which the inner image layer 152, the arbitrary image layer 151, and the outer image layer 153 are connected to each other discontinuously or continuously for a first section F1 including the anterior, a second section F2 including the canine, and a third section F3 including the molar. For reference, an interpolation method can be used to obtain a continuous final image layer by connecting the image layer of each section.

As described above, a specific method where the single image layer is obtained by using a plurality of image layers of each section and the panoramic X-ray image is obtained by reconstructing the panoramic X-ray image of the final image layer can be referred to in the document of Korean Patent No. 10-1094180 by the applicant of the present invention. Here, as in the mentioned description, the panoramic X-ray image for a plurality of image layers may be separately reconstructed, that is, may be reconstructed based on different X-ray image data, or the panoramic X-ray images for a plurality of image layers may be reconstructed by using the X-ray image data of the panoramic X-ray image for the arbitrary image layer. A specific method for the latter can be referred to in the document of Korean Patent No. 10-0917679 by the applicant of the present invention, and a specific method of the former can be referred to in FIG. 10 and the related description.

Herein, for the convenience of description, the number of divided sections and the number of image layers set in advance are each simplified to three. However, in the actual apparatus, the unit section for performing the auto-focusing operation may be subdivided into a larger number of sections along the longitudinal direction of the dental arch, and also may be subdivided into a plurality of areas in the height direction of the teeth perpendicular to the drawing. Further, the number of image layers preset to the inside and outside of the arbitrary image layer 151 may be larger.

Figure 9:
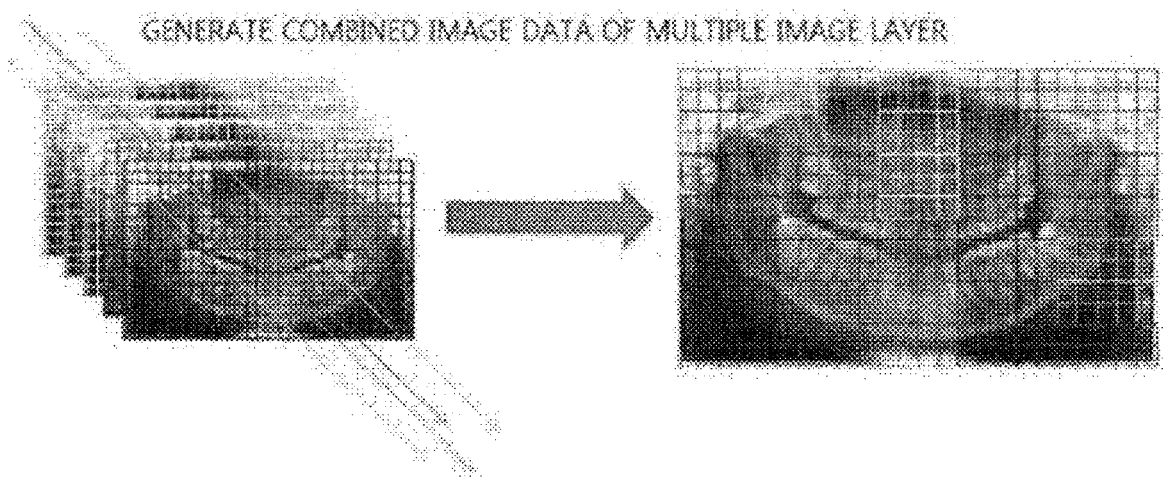
FIG. 9 shows another example of the first panoramic X-ray image displayed on the display screen according to the embodiment of FIG. 4.

FIG. 9 shows another example of the first panoramic X-ray image displayed on the display screen according to the embodiment of FIG. 4.

The first panoramic X-ray image may be panoramic X-ray images of a plurality of image layers, the clearest block image by comparing the image data of a plurality of image layers in block unit, or a panoramic X-ray image reconstructed by combining block image data. In this case, the first image layer may be a combination of block unit image layers selected from a plurality of image layers.

Looking more closely at these examples, first, panoramic X-ray images of a plurality of image layers are shown on left right side of the drawing.

Here, the panoramic X-ray image for a plurality of image layers may be separately reconstructed, that is, may be reconstructed based on different X-ray image data, or the panoramic X-ray images for a plurality of image layers may be reconstructed by using the X-ray image data of the panoramic X-ray image for the arbitrary image layer. A specific method for the latter can be referred to in the document of Korean Patent No. 10-0917679 by the applicant of the present invention, and a specific method of the former can be referred to in FIG. 11 and the related description.

The panoramic X-ray images for a plurality of image layers are reconstructed into panoramic X-ray images of the same scale, that is, the same magnification, the panoramic X-ray images are partitioned into block groups of unit blocks of the same number and size, and then the block image with the sharpest image of each unit block is selected through frequency analysis, etc. Further, the first panoramic X-ray image on the right side can be obtained by combining these block images. In this case, the first image layer may be a combination of block unit image layer that is closest to the locus of the dental arch of the actual subject over the entire block. In FIG. 9, the block image is selected from the panoramic X-ray images of a plurality of image layers for the convenience of description, but it is also possible to select block image data from panoramic X-ray image data for a plurality of image layers.

A specific method for obtaining the final panoramic X-ray image by combining and reconstructing panoramic X-ray images of a plurality of image layers, the block unit image selected from image data of a plurality of image layers, or the block unit image data can be referred to the document of Korean Patent No. 10-1664166, and the document of Korean Patent No. 10-1389841 by the applicant of the present invention.

Figure 10:
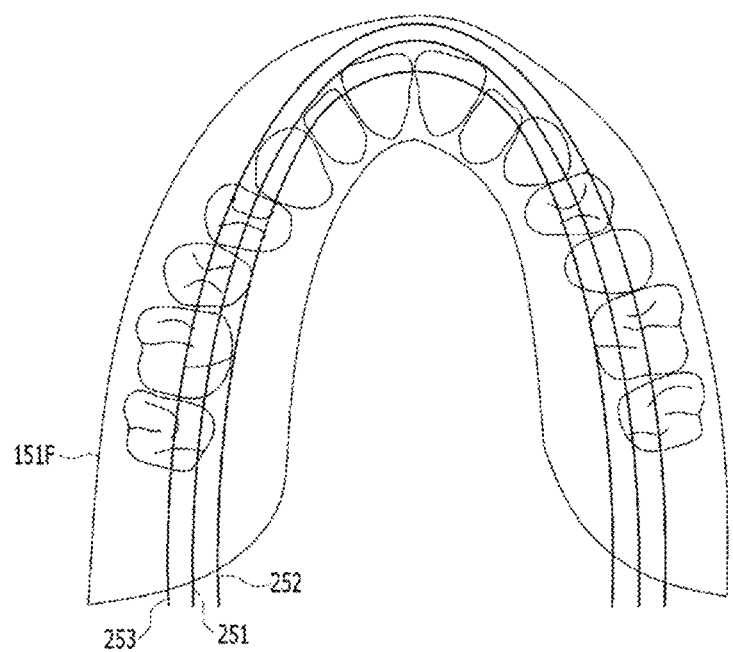
FIG. 10 shows an example of the second image layer of the second panoramic X-ray image displayed on the display screen according to the embodiment of FIG. 4.

FIG. 10 shows an example of the second image layer of the second panoramic X-ray image displayed on the display screen according to the embodiment of FIG. 4.

A second image layer 251, 252, 253 may be one or more image layers. Meanwhile, preferably, the second image layer 251, 252, 253 may be set in advance and stored in the image processor. For example, a plurality of second image layers 251, 252, and 253 may include an arbitrary image layer 251 and inner and outer image layers. The plurality of second image layers 251, 252, and 253 may be set not to intersect each other. Here, the second image layers 251, 252, and 253 may be reconstructed separately, i.e., as different X-ray image data, or may be reconstructed as X-ray image data for the arbitrary image layer.

Figure 11:
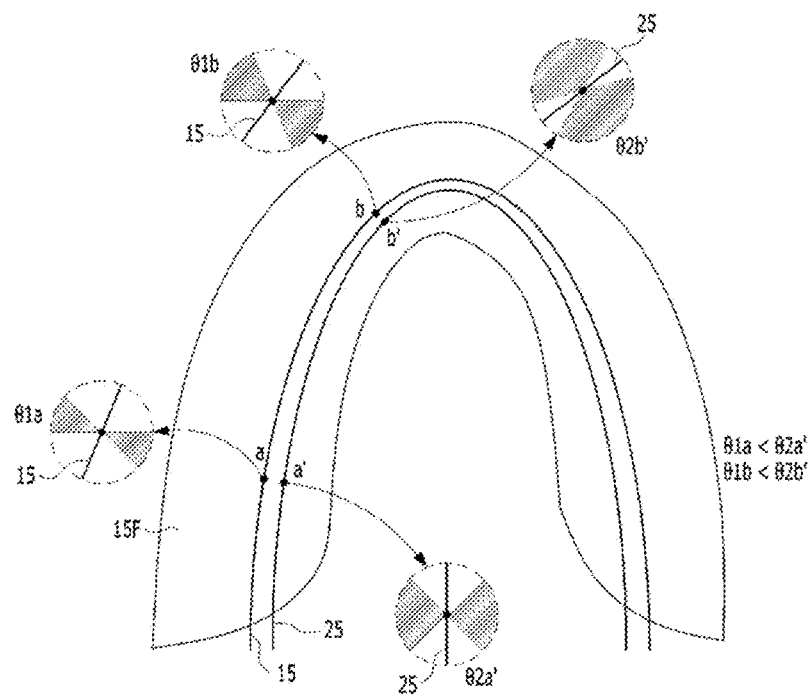
FIG. 11 shows an angle range of X-ray image data used in reconstructing the first panoramic X-ray image and the second panoramic X-ray image.

FIG. 11 shows an angle range of X-ray image data used in reconstructing the first panoramic X-ray image and the second panoramic X-ray image. For reference, the following description of FIG. 11 is an example of implementing the first and second image layers, which may be applied to the first and second image layers previously described with reference to FIGS. 5 to 10.

As described above, the X-ray image display apparatus according to the present invention may be configured such that a plurality of frame-by-frame X-ray image data obtained from the X-ray sensor through a single scan sequence is stored in the storage, and X-ray image data required for reconstructing the panoramic X-ray image of the arbitrary image layer is extracted from the storage and then is directly back-projected into the arbitrary image layer, whereby it is possible to reconstruct the panoramic X-ray image, which is different from the conventional shift-and-add method of implementing image layers by superimposing X-ray image data. Here, the X-ray image data required for reconstructing the panoramic X-ray image of the arbitrary image layer may be X-ray image data in a predetermined angle range passing through each point of the image layer, and if necessary, some of the X-ray image data in the predetermined angle range passing through each point of the arbitrary image layer may be calculated by interpolating other X-ray image data.

However, when the panoramic X-ray image is reconstructed in the above manner, there is a difference in the depth resolution of the panoramic X-ray image according to the angle range of the X-ray image data passing through each point of the image layer.

To be more specific, if only one angle of the X-ray image data is used for an arbitrary point in the image layer, then all the structures on the X-ray path of the X-ray image at that angle are superimposed on one plane, whereby only X-ray images without depth resolution can be obtained. However, if X-ray image data of various angles are used for the corresponding point, a panoramic X-ray image with an improved depth resolution can be obtained, that is, a panoramic X-ray image of a thinner image layer with respect to the X-ray transmission direction can be obtained, and as the angle range of the X-ray image data passing through each point of the image layer is increased, the depth resolution is improved.

In the drawing, the first image layer 15 is, for example, an arbitrary image layer, and reference numeral 15F designates an imaging area. The X-ray image display apparatus according to the embodiment is configured such that for each point of the first image layer 15, the first panoramic X-ray image is reconstructed by using the X-ray image data of a predetermined angle range passing through the points. For example, X-ray image data in angle range θ1$a$ may be used for point a on the first image layer 15, and X-ray image data in angle range θ1$b$ may be used for point b.

Further, in the drawing, as an example, the second image layer 25 is set to lie side by side on the inside of the first image layer 15. Further, the X-ray image display apparatus according to the embodiment is configured such that for each point of the second image layer 25, the second panoramic X-ray image is reconstructed by using the X-ray image data of a predetermined angle range passing through the points. For example, X-ray image data in angle range θ2$a$' may be used for point a' on the second image layer 25, and X-ray image data in angle range θ2$b$' may be used for point b'.

Herein, the point a' may be the point at which the normal passing through the point a in the first image layer 15 intersects the second image layer 25. In other words, the point a' and the point a follow the same x-ray irradiation direction. Similarly, the point b' may be the point at which the normal passing through the point b in the first image layer 15 intersects the second image layer 25. In other words, the point b' and the point b follow the same x-ray irradiation direction. Here, θ1$a$ and θ2$a$', and θ1$b$ and θ2$b$' have the following relationship: θ1$a$<θ2$a$', and θ1$b$<θ2$b$'. Thereby, the second panoramic X-ray image of the second image layer 25 has better depth resolution than the first panoramic X-ray image of the first image layer 15. In other words, the second image layer 25 has a thickness thinner than that of the first image layer 15.

Here, the first and second image layers 15 and 25 may show the same locus, but they have different thicknesses, so they appear as different panoramic X-ray images visually.

As described above, the X-ray image display apparatus according to the present invention may be configured such that X-ray image data penetrating each point of the arbitrary image layer in a predetermined angle range is obtained from X-ray image data of multiple frames at different angles, and the X-ray image data penetrating each point in the predetermined angle range is directly back-projected into each point of the arbitrary image layer, whereby it is possible to reconstruct a panoramic X-ray image of an image layer. Here, particularly, the user can freely select the quantity, angle, position, and shape of the arbitrary image layer regardless of external factors such as the imaging locus of the apparatus. Of course, the thickness of the image layer can be freely selected according to the angle range of the X-ray image data penetrating each point of the image layer. This is applicable to both the first and/or second panoramic X-ray image reconstruction, so that the depth resolution of the first and/or second panoramic X-ray image can be freely adjusted.

In the above description, the depth resolution of the second panoramic X-ray image for the second image layer is superior to the depth resolution of the first panoramic X-ray image for the first image layer, but the opposite case is also possible. Both the first and second panoramic X-ray images may have excellent depth resolution compared to the conventional panoramic X-ray image, and both the first and second panoramic X-ray images may have lower depth resolution than the conventional panoramic X-ray image. In other words, the depth resolution of the first and second panoramic X-ray images can be determined entirely by the user's choice.

Figure 12:
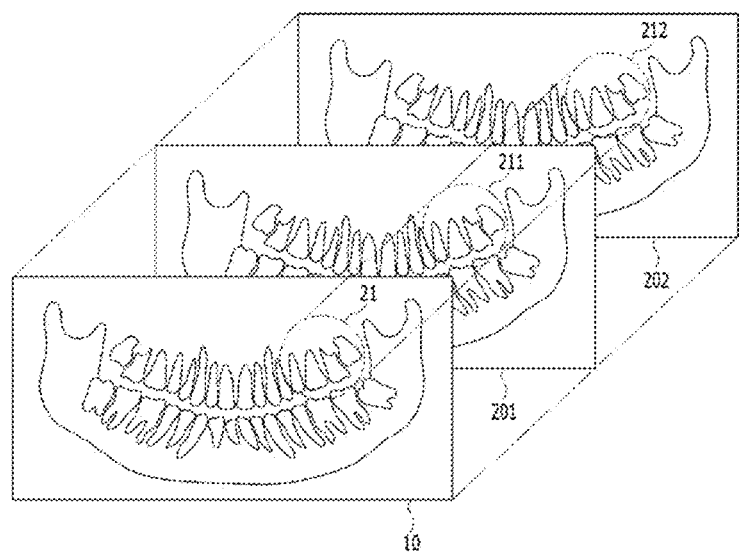
FIG. 12 shows an alignment relationship between the first panoramic X-ray image and the second panoramic X-ray image.

FIG. 12 shows an alignment relationship between the first panoramic X-ray image and the second panoramic X-ray image. For convenience, the first panoramic X-ray image is one, and the second panoramic X-ray image is two in number.

As shown in the drawing, second panoramic X-ray images 201 and 202 are stored as panoramic X-ray images of the same frame size and the same magnification, representing the same magnification in the same range as the first panoramic X-ray image 10 on the plane. However, in the display screen shown in FIG. 4, only portions 211 and 212 of the second panoramic X-ray images 201 and 202 corresponding to the partial image display part 21 are displayed on the screen. The displayed method may be as follows: the portions 211 and 212 corresponding to the partial image display part 21 in one or more second panoramic X-ray images are displayed by replacing the portion corresponding to the partial image display part 21 or superimposing thereon, wherein it may be up to the user to choose which of the second panoramic X-ray images 201 and 202 is displayed on the partial image display part 21.

Figure 13A:
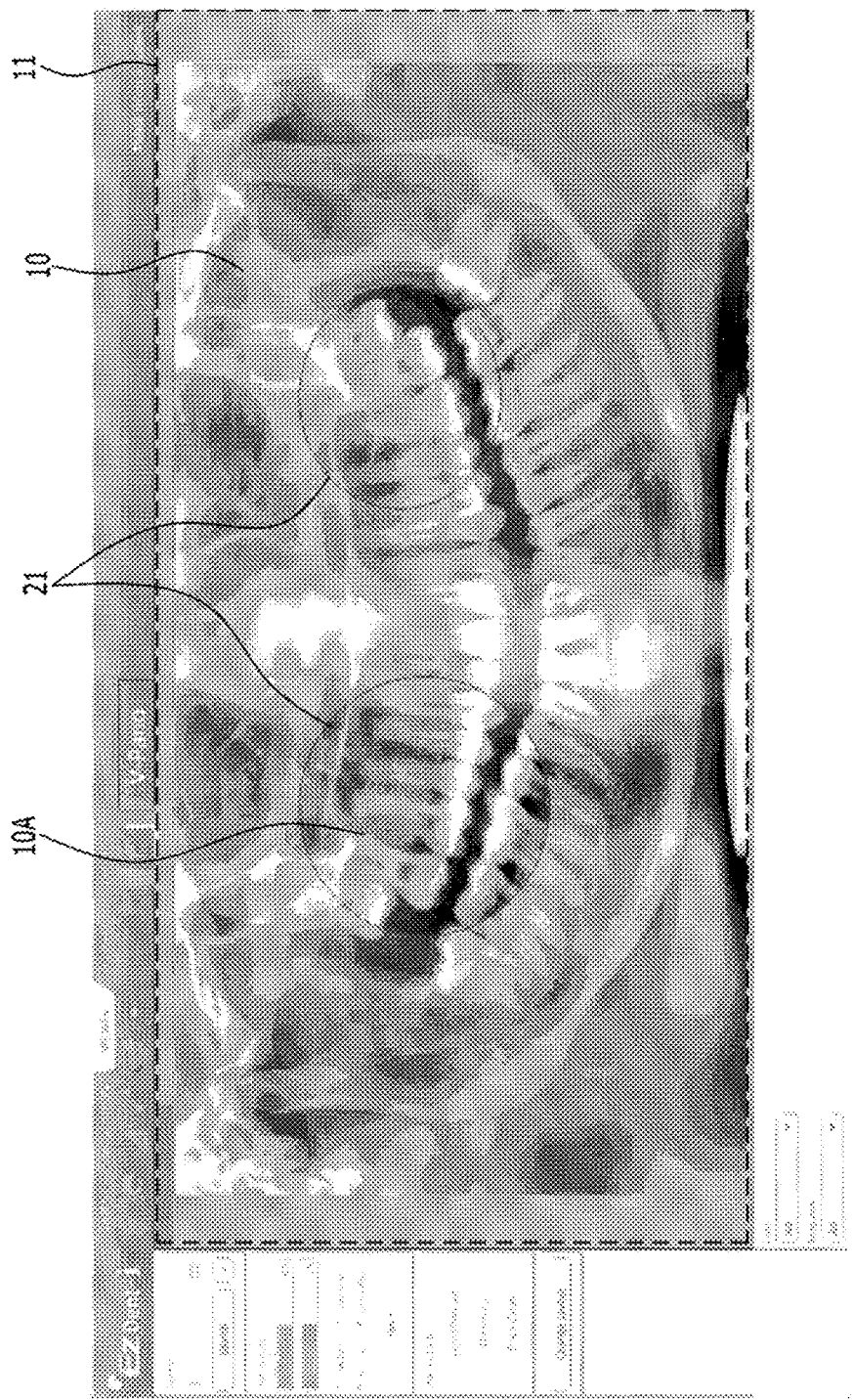
FIGS. 13a and 13b comparatively show the first and second panoramic X-ray images displayed on the display screen according to the embodiment of FIG. 4.
Figure 13B:
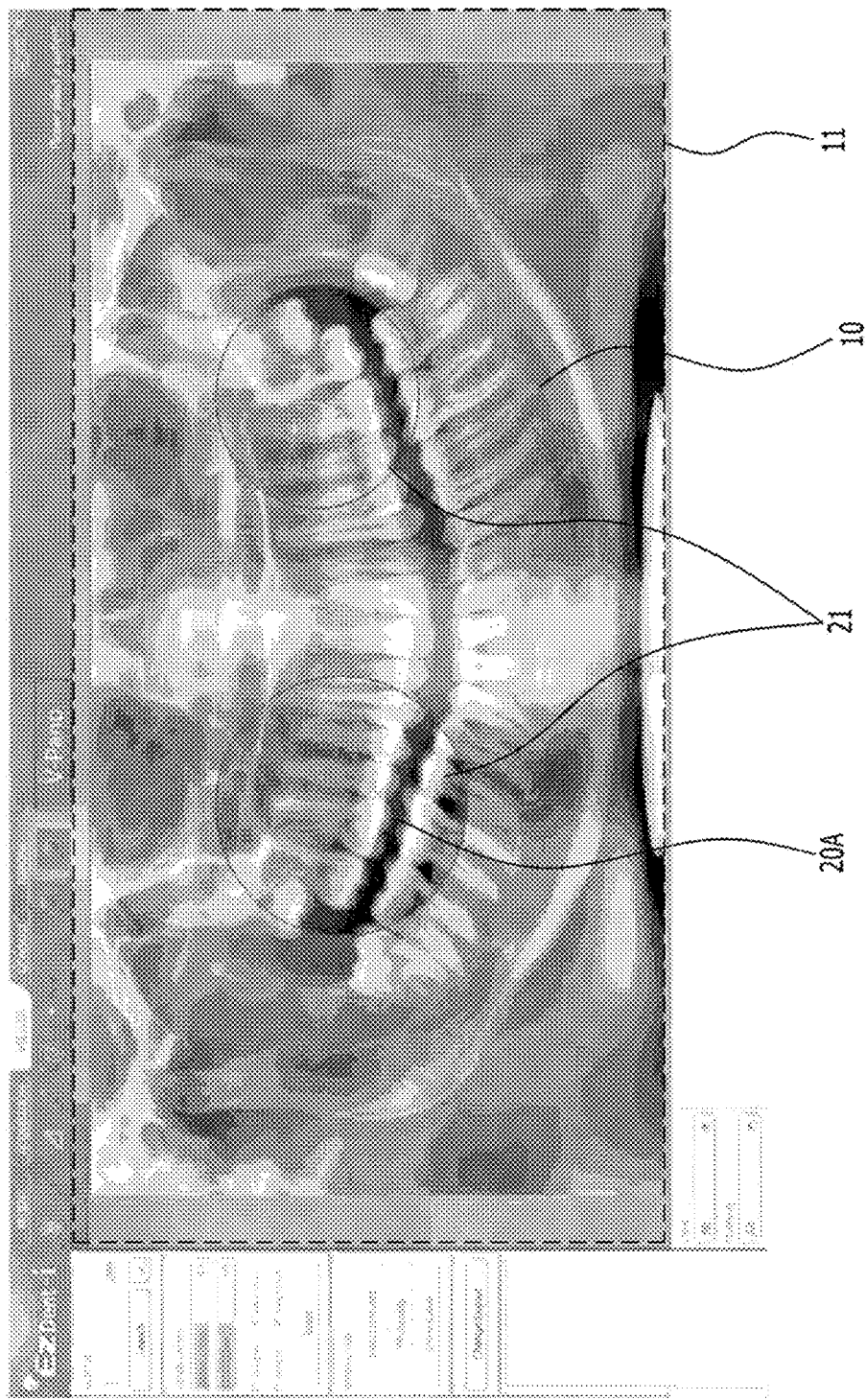

FIGS. 13$a$ and 13$b$ comparatively show the first and second panoramic X-ray images displayed on the display screen according to the embodiment of FIG. 4.

For convenience, in FIGS. 13$a$ and 13$b$, the image in the partial image display part 21 is converted into a corresponding partial image of a first panoramic X-ray image 10A (see FIG. 13$a$) or a second panoramic X-ray image 20A (see FIG. 13$b$) according to the user's input in the state where the image displayed on the background image display part 11 is maintained. In FIGS. 13$a$ and 13$b$, the difference between two partial image display parts 21 can be easily found by comparing the parts indicated by the arrows on the left side. In FIG. 13$a$, the corresponding portion of the first panoramic X-ray image 10A is displayed in the partial image display part 21 so that the dental root of the maxillary molar appears as one. On the other hand, in FIG. 13$b$, the corresponding portion of the second panoramic X-ray image 20A is displayed on the partial image display part 21 on the same side so that the dental root of the maxillary molar appears as two.

As described above, the user may select the second image layer of the second panoramic X-ray image displayed on the partial image display part 21 through an input action such as turning the mouse wheel, as an example of the input unit, forward/backward in the activated state of the partial image display part 21.

Figure 14:
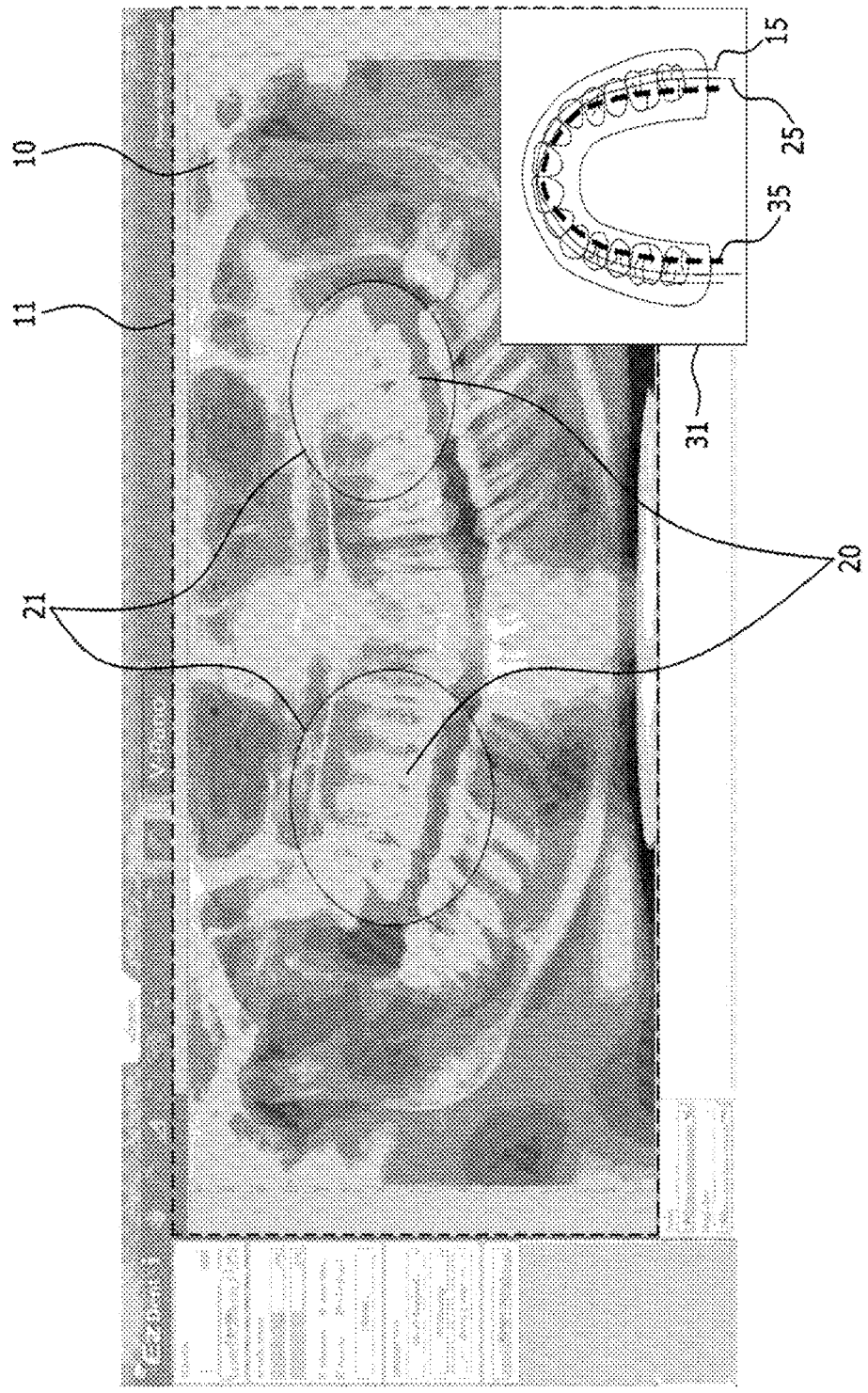
FIG. 14 shows another example of the display screen of the X-ray image display apparatus according to the present invention.

FIG. 14 shows another example of the display screen of the X-ray image display apparatus according to the present invention.

Compared to the embodiment of FIG. 4, the embodiment is different in that it further includes an indicator display part 31 indicating which image layer is shown by the second panoramic X-ray image 20 displayed on the partial image display part 21 of the display screen. The indicator display part 31 is capable of displaying the quantity, thickness, angle, shape, position, and the like of the first image layer 15 of the first panoramic X-ray image 10 and/or the second image layer 25 of the second panoramic X-ray image 20 as at least one of numbers, pictures, and figures. This allows the user to intuitively recognize the relative relationship of the first and second image layers of the first and second panoramic X-ray images displayed on the display screen. In the drawing, as an example, the indicator display part 31 indicates that an image layer 35 designated by reference numeral 35 is being displayed on the partial image display part 21.

As described above, the X-ray image display apparatus according to the present invention simultaneously displays the first panoramic X-ray image of at least one first image layer, and a portion of the second panoramic X-ray image that includes at least one first image layer or a portion of the second panoramic X-ray image of at least one second image layer that is at least partially different or completely different from the first image layer through the display screen. Here, since the first and second panoramic X-ray images show the same magnification, relative locations with respect to the dental arch are displayed aligned with each other, and the second panoramic X-ray image is displayed as part of it, wherein the second panoramic X-ray image may be displayed by being superimposed on the first panoramic X-ray image or by partially replacing the first panoramic X-ray image.

Next, in the X-ray image display apparatus according to the present invention, a process of from acquiring X-ray image data to displaying first and second panoramic X-ray images will be described as an example.

Figure 15:
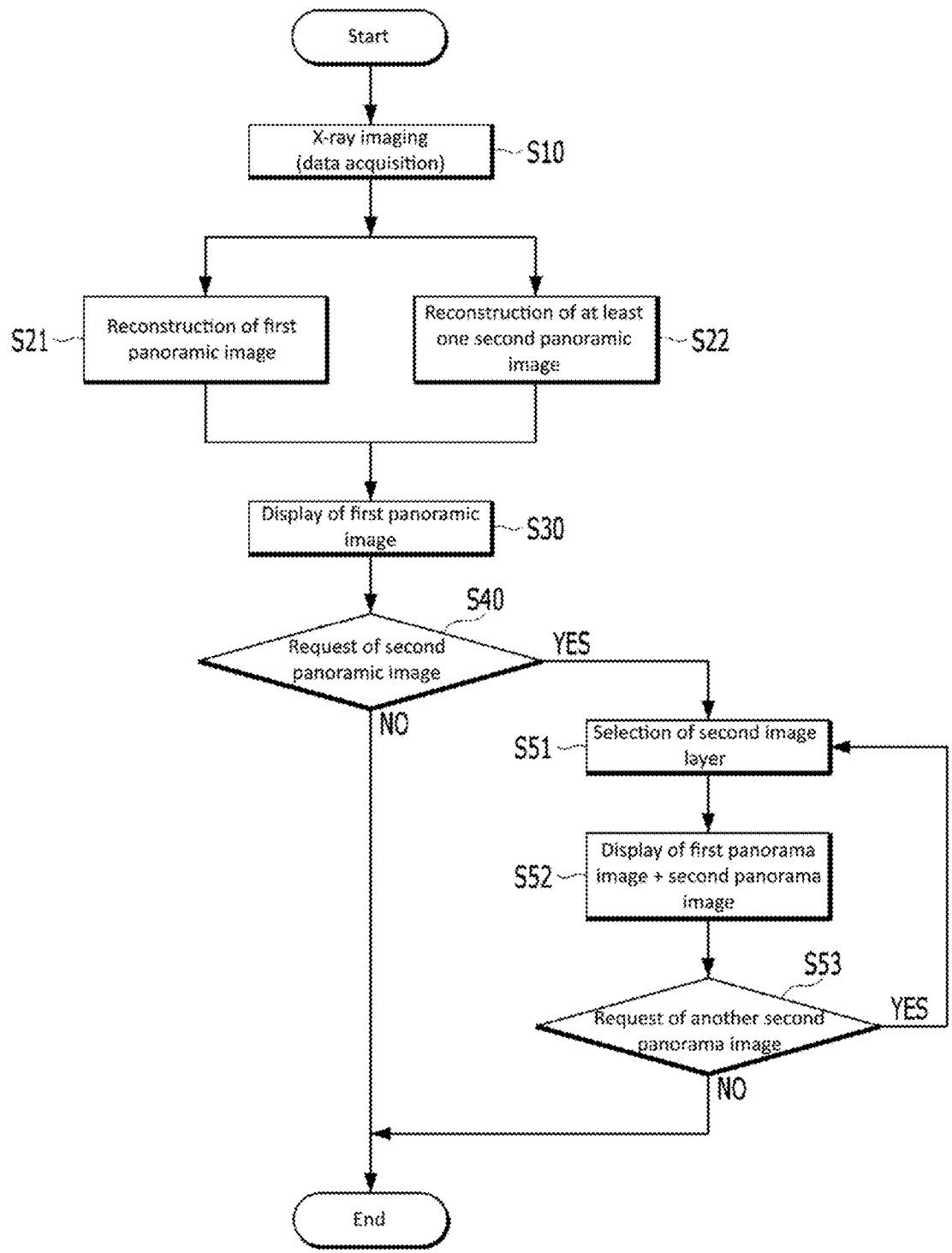
FIG. 15 shows an operation process of the X-ray image display apparatus according to the present invention.

FIG. 15 shows an operation process of the X-ray image display apparatus according to the present invention.

Firstly, X-ray imaging is performed by the imaging unit (s10). This involves a preset motion of the imaging unit, including an X-ray generator and an X-ray sensor. The motion of the imaging unit may include a series of consecutive movements of the X-ray generator and the X-ray sensor rotating while facing each other with the subject interposed therebetween (the direction of the movement such as rotation direction is not limited to one direction). The movement of the X-ray generator and the X-ray sensor synchronized with the above movement constitutes one scan sequence. X-ray image data of multiple frames acquired through the scan sequence is stored in the storage. The X-ray image data of multiple frames may include information such as a position and a direction where an X-ray beam forming each frame penetrates the subject.

Then, in the image processor, reconstruction of the first panoramic X-ray image is performed (s21) and reconstruction of the second panoramic X-ray image is performed (s22). The process where the image processor extracts the data required for each panoramic X-ray image from the X-ray image data of multiple frames stored in the storage and reconstructs the first and second panoramic X-ray images, particularly, the process of reconstructing the first and/or second panoramic X-ray image with the enhanced depth resolution is as described with reference to FIG. 9. The first and second panoramic X-ray images reconstructed in the image processor are also stored in the storage.

The viewer module displays the first panoramic X-ray image on the background image display part (s30). Here, by determining whether the user requests the second panoramic X-ray image for a part of the first panoramic X-ray image through the input unit (s40), the second panoramic X-ray image for the part and the first panoramic X-ray image may be displayed simultaneously (s52). If the second panoramic X-ray image is provided by default, the process of determining whether the second panoramic X-ray image is requested (s40) may be omitted. Meanwhile, before displaying the second panoramic X-ray image, a step of selecting the position, angle, quantity or thickness of the second image layer to be displayed as the second panoramic X-ray image may be performed (s51). After the arbitrary second panoramic X-ray image is displayed, it is determined whether another second panoramic X-ray image is requested (s53), and if requested, the second panoramic X-ray image of the second image layer of another position, shape, and thickness may be displayed again along with the first panoramic X-ray image (s52) through selection of another second image layer (s51).

FIGS. 16 to 20 show other examples of the display screen according to the operation process of the X-ray image display apparatus according to the present invention.

Figure 16:
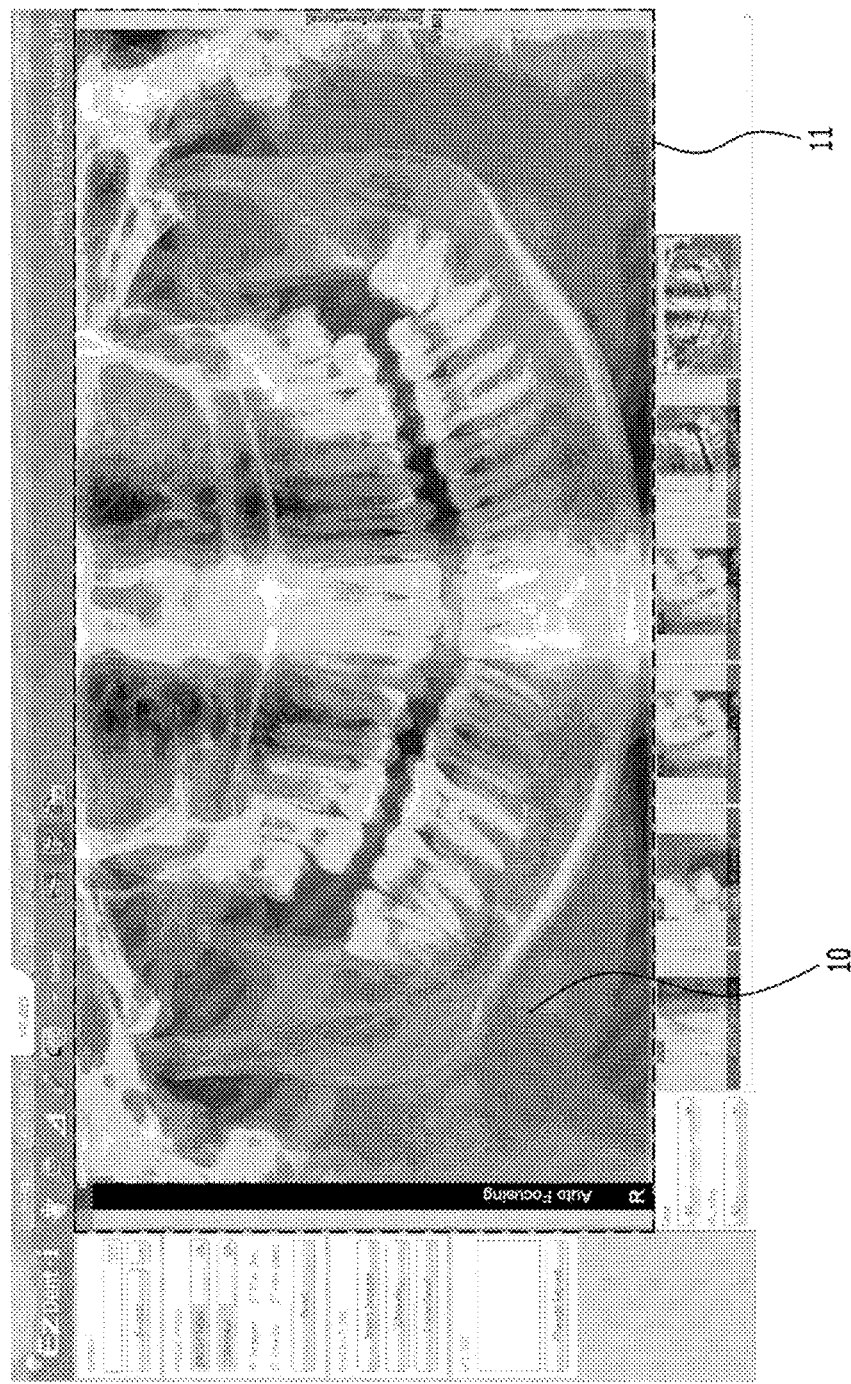
FIGS. 16 to 20 show other examples of the display screen according to the operation process of the X-ray image display apparatus according to the present invention.

As shown in FIG. 16, the viewer module provides the background image display part 11 which displays the first panoramic X-ray image 10 on the display screen, and may display the first panoramic X-ray image 10 on the background image display part. Here, the first panoramic X-ray image 10 may be an image where panoramic X-ray images of multiple image layers with the same magnification are superimposed onto each other.

Figure 17:
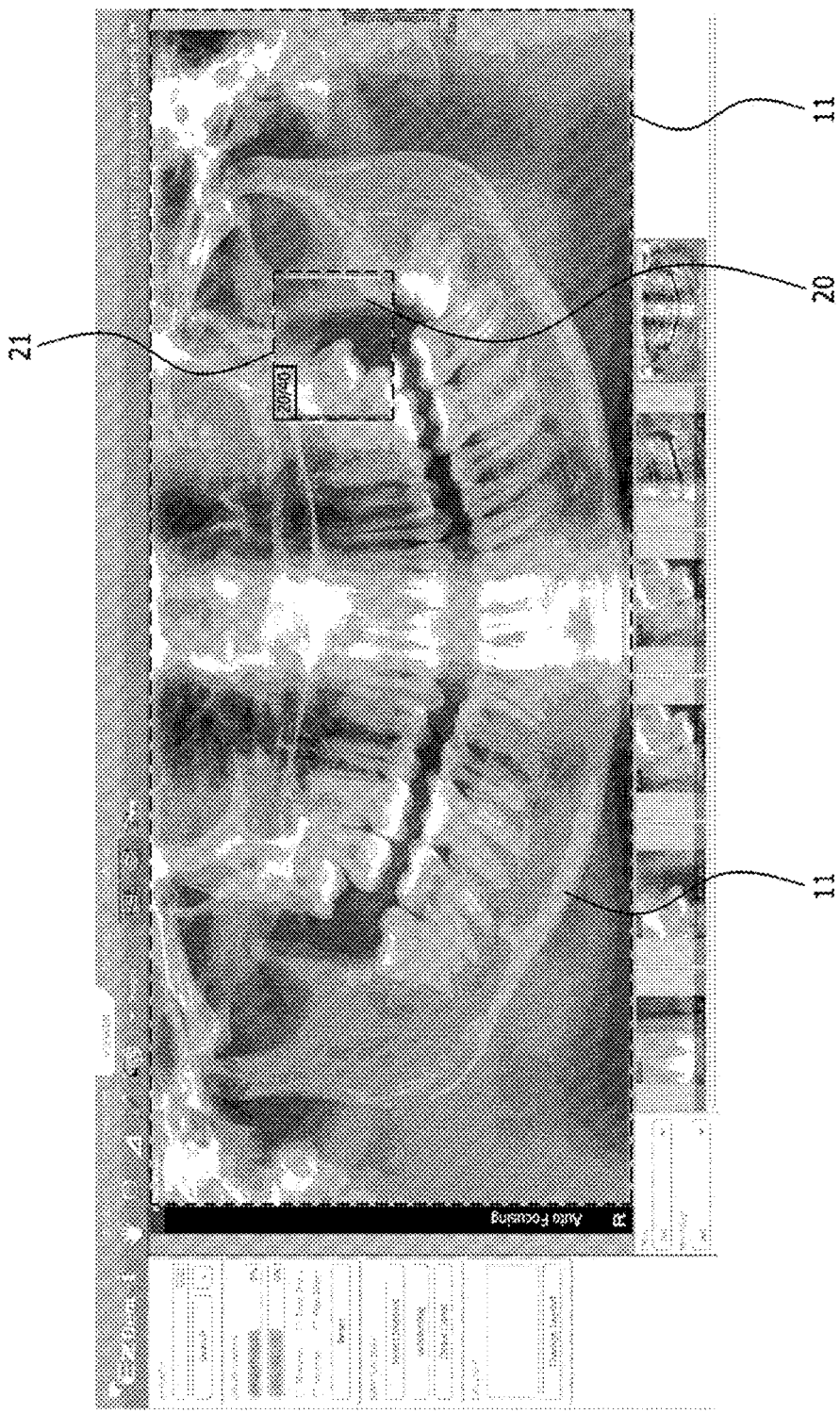
Figure 18:
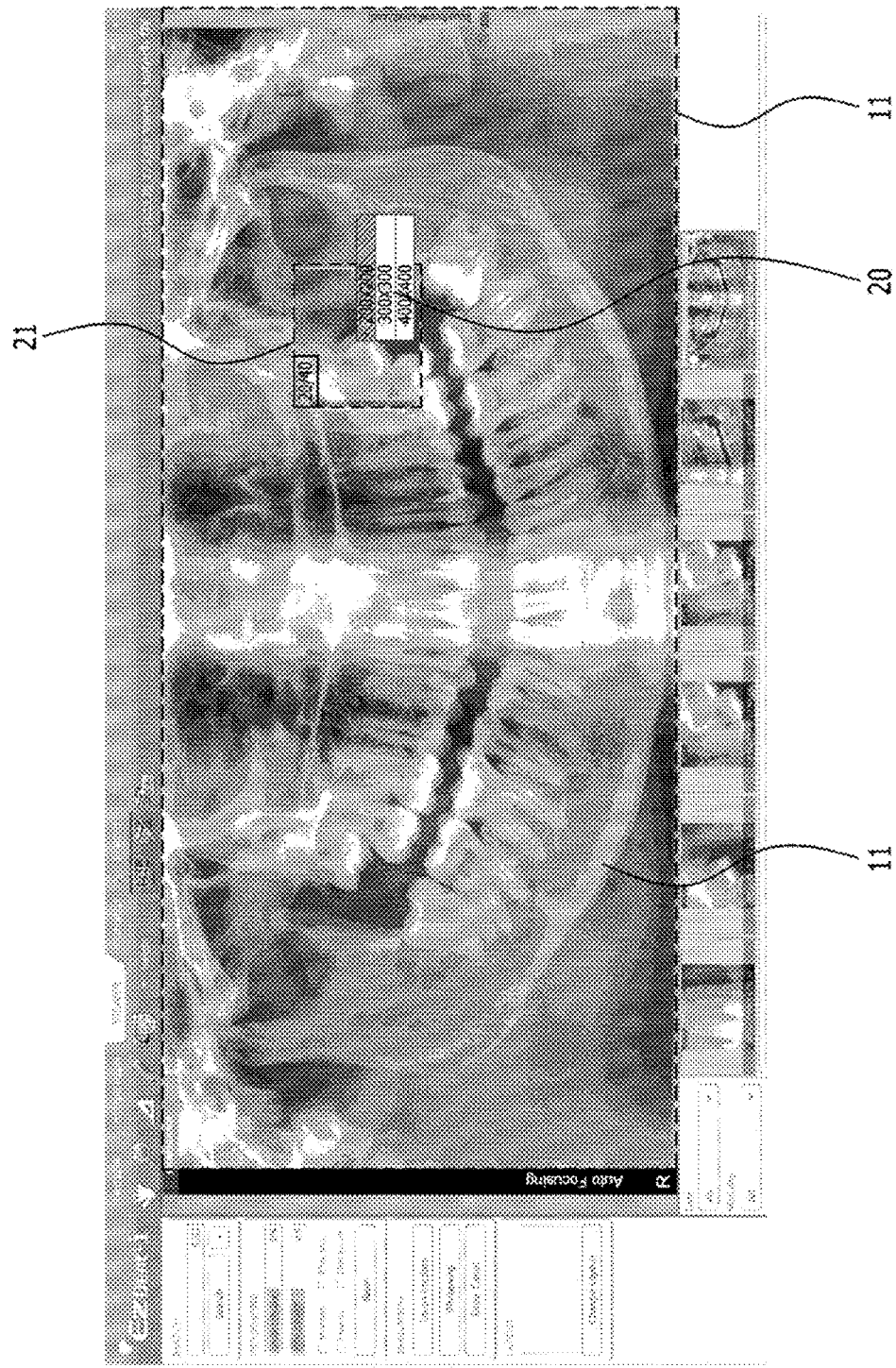

Then, as shown in FIG. 17, the partial image display part 21 is activated at a predetermined portion of the first panoramic X-ray image 10 according to the user's selection, and the second panoramic X-ray image 20 may be displayed thereon. Here, the second panoramic X-ray image 20, which corresponds to a predetermined portion of the first panoramic X-ray image 10, replaces the predetermined portion of the first panoramic X-ray image 10 or is superimposed onto the same. Further, in this state, the user can freely move and adjust the position of the partial image display part 21 and adjust the size of the partial image display part 21. FIG. 18 shows that the size of the partial image display part 21 is adjusted according to the user's selection. During this process, the viewer module displays the second panoramic X-ray image 20 for the corresponding part of the first panoramic X-ray image 10 on the partial image display part 21 in real time.

Here, preferably, the second panoramic X-ray image 20 may be a panoramic X-ray image for one of the image layers of the first panoramic X-ray image 10. In this case, as shown in FIG. 18, the viewer module may display an indicator indicating the relative positional relationship between the panoramic X-ray image superimposed onto the first panoramic X-ray image 10 and the second panoramic X-ray image 20 currently displayed on the partial image display part 21.

As an example, 20/40 shown in the drawing means that the number of the panoramic X-ray images superimposed onto the first panoramic X-ray image 10 is 40, and when the serial number is given from the front to the back on the screen, the second panoramic X-ray image 20 displayed on the current partial image display part 21 is the 20th. Further, the red square indicates the number of panoramic X-ray images superimposed onto the first panoramic X-ray image 10 as a height, and the relative position of the second panoramic X-ray image 20 displayed on the current partial image display part 21 as a red line.

Figure 19:
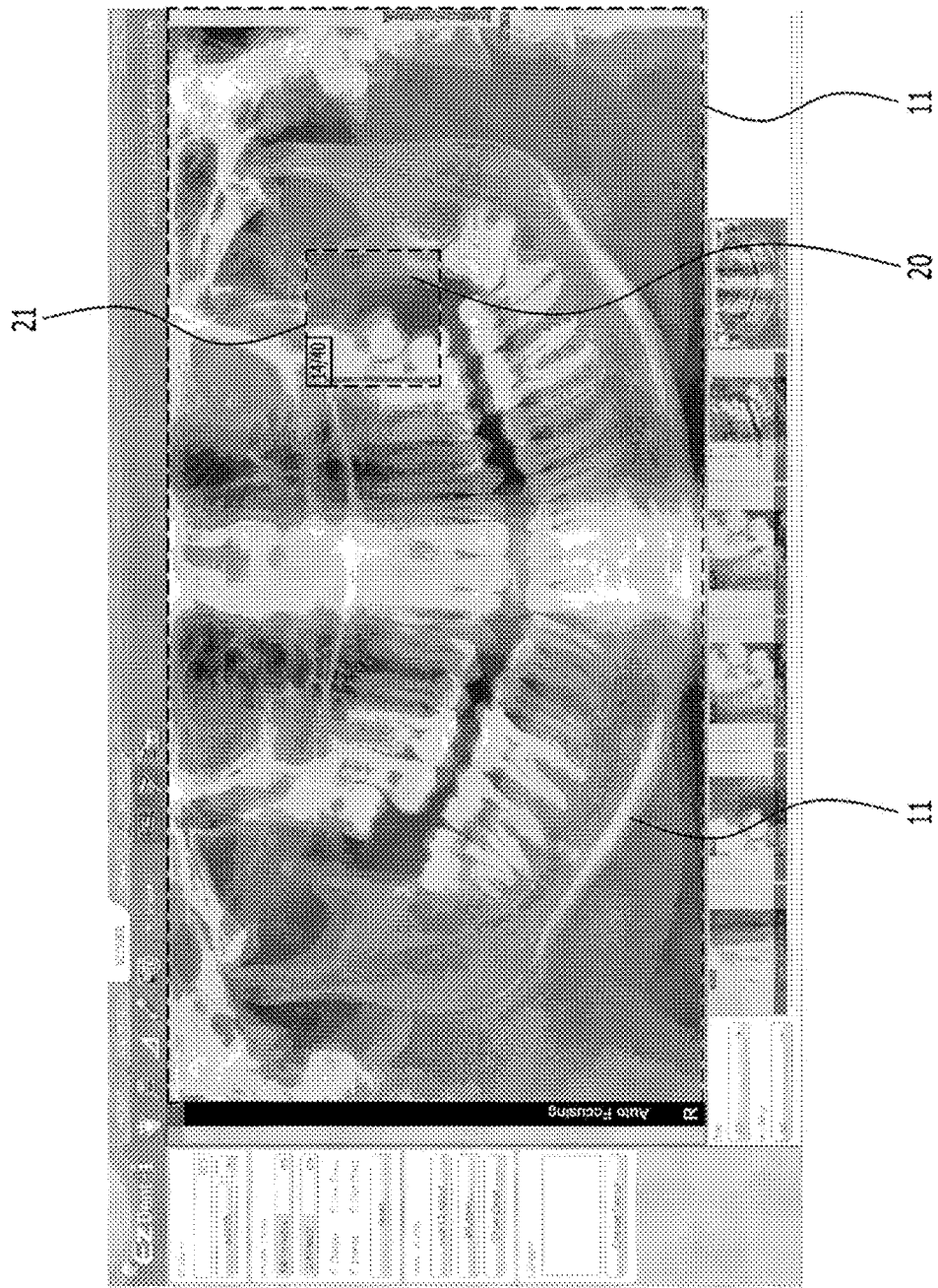

Further, the viewer module may switch the second panoramic X-ray image 20 displayed on the partial image display part 21 according to the user's manipulation, such as rotating the mouse wheel. FIG. 19 shows the second panoramic X-ray image 20 on the partial image display part 21 switched from the state of FIG. 18 by the user's manipulation, wherein the panoramic X-ray image of the 14th image layer among the 40 panoramic X-ray images superimposed on the first panoramic X-ray image 10 is displayed as the second panoramic X-ray image 20. Compared to FIG. 17, the second panoramic X-ray image 20 is changed, which means that the second image layer of the second panoramic X-ray image 20 has been changed.

Figure 20:
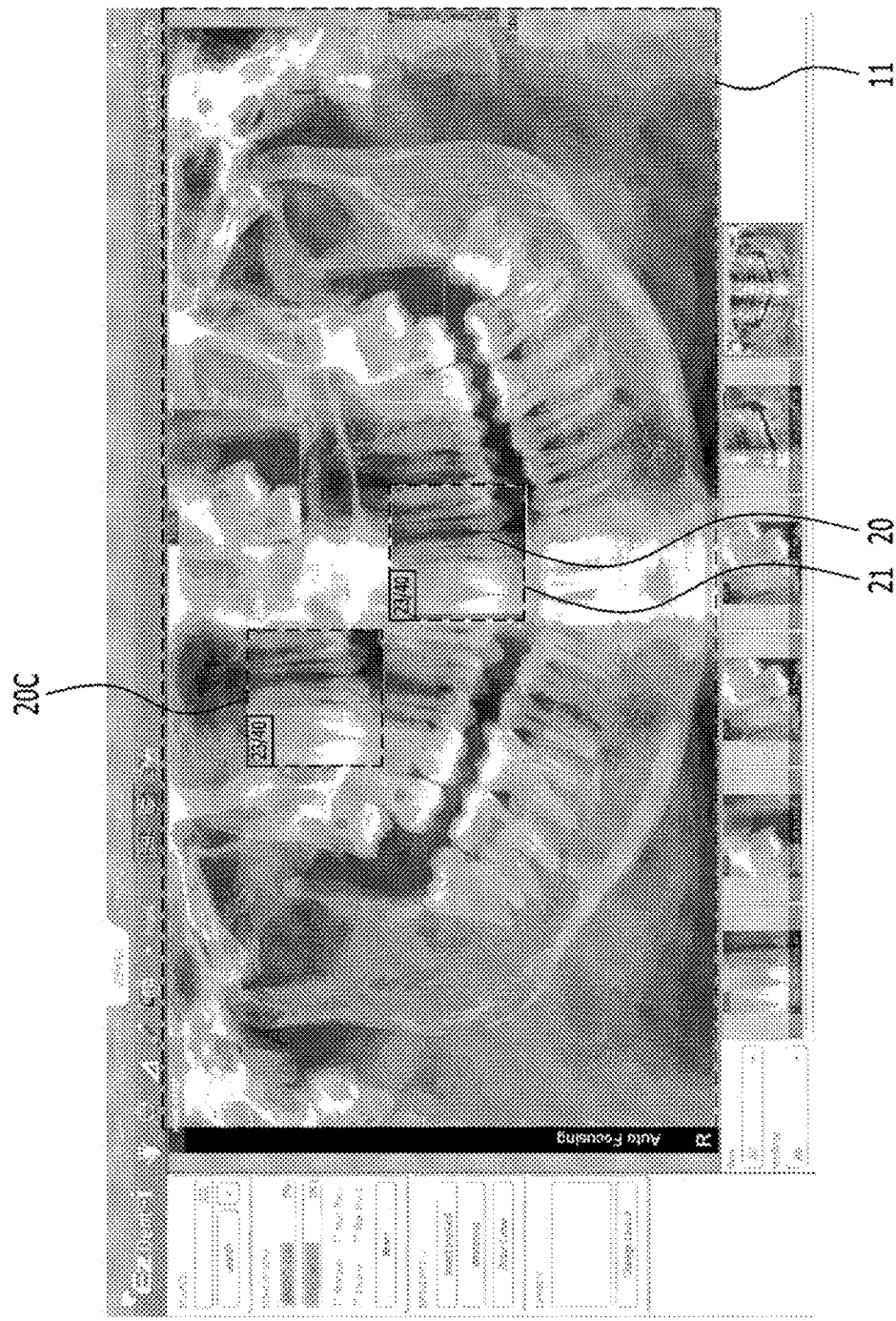

Further, the viewer module may provide a capture screen 20c of the second panoramic X-ray image 20 displayed on the partial image display part 21 according to the user's manipulation such as double-clicking. FIG. 20 shows the above function, wherein the capture screen 20c of the second panoramic X-ray image 20 for the first part is displayed in association with the first part, and the partial image display part 21 displays the second panoramic X-ray image 20 at another position by the user manipulation.

Further, such a capture screen 20c may be stored as a separate image file.

Hereinbelow, reference will be made to the case where the first X-ray image of the X-ray image display apparatus according to the present invention is a cephalometric X-ray image, and for convenience, the point different from the above description will be mainly discussed.

Figure 21:
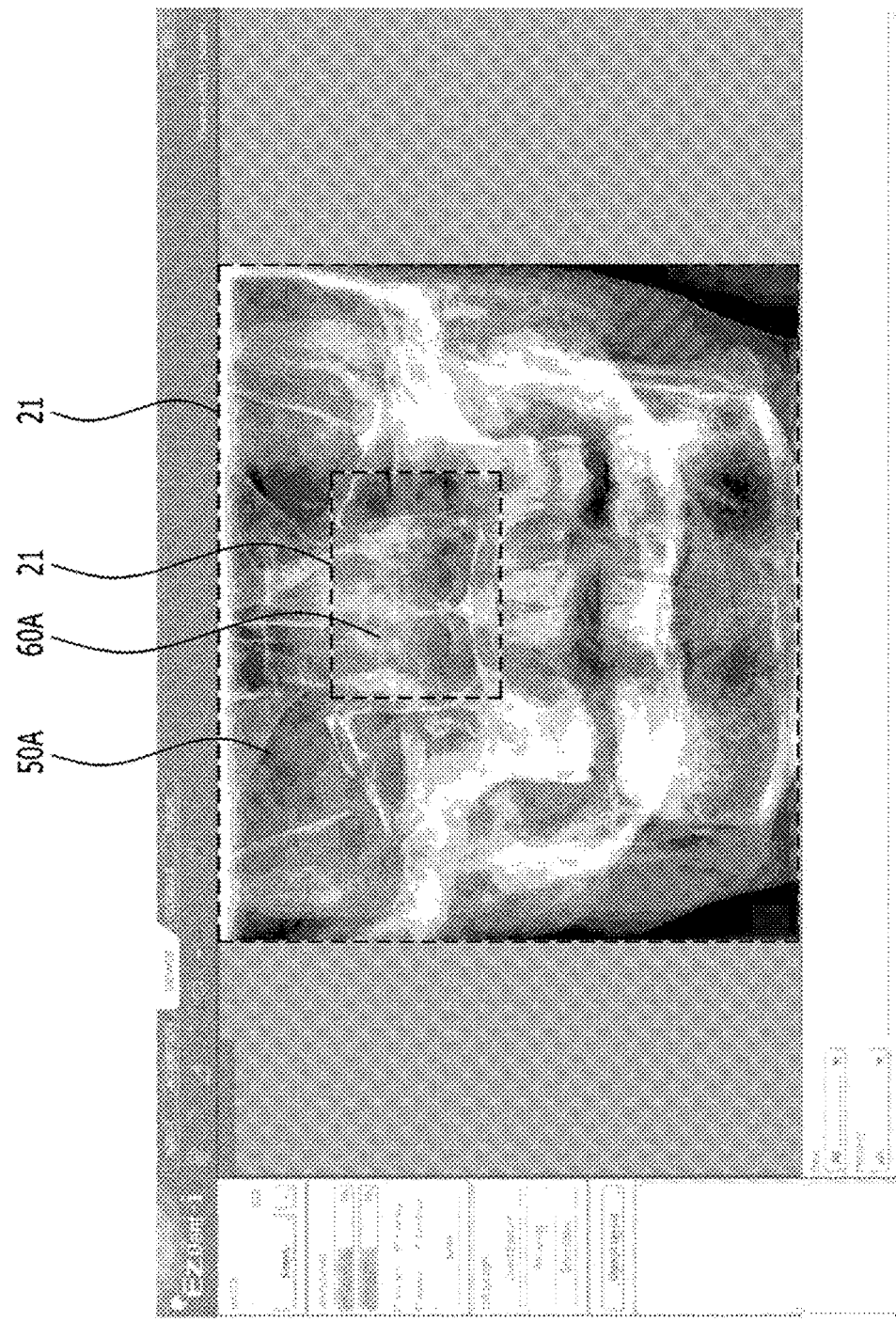
FIG. 21 shows a further example of the display screen of the X-ray image display apparatus according to the present invention.

FIG. 21 shows a further example of the display screen of the X-ray image display apparatus according to the present invention. See also FIG. 4.

The screen output through the X-ray image display apparatus according to an embodiment of the present invention is provided with the background image display part 11 displaying a cephalometric X-ray image as a first X-ray image 50A, and is also provided with the partial image display part 21 disposed at a predetermined portion of the background image display part 11 and configured to display a portion of a tomographic X-ray image of at least one image layer in the cephalometric X-ray image as a second X-ray image 60A corresponding to the predetermined portion.

The partial image display part 21 may be provided one or more in number, and according to the user's input, for example, through a mouse input, the size, position, shape or quantity of the partial image display part 21 may be adjusted. Further, the partial image display part 21 may be configured such that a user (e.g., a dentist) first checks the cephalometric X-ray image provided through the background image display part 11, and when it is necessary to further review a predetermined part, the predetermined part is selectively activated according to the user's instructions, and the corresponding tomographic X-ray image of an arbitrary image layer in the cephalometric X-ray image may be displayed by superimposing on the cephalometric X-ray image of that part or by replacing the cephalometric X-ray image of that part. Further, the border between the cephalometric X-ray image and the tomographic X-ray image may be displayed by displaying the edge of the partial image display part 21 on the screen.

The cephalometric X-ray image and the tomographic X-ray image may be respectively reconstructed by using at least a part of a plurality of X-ray data obtained through a single scan sequence of the X-ray generator 311 and the X-ray sensor 312. Further, of a plurality of X-ray frame data, the first group of X-ray frame data for the cephalometric X-ray image and the second group of X-ray frame data for the tomographic X-ray image may be at least partially different from each other.

To achieve this, the X-ray generator 311 and the X-ray sensor 312 respectively irradiates and receives X-rays while moving along a predetermined locus with the subject's head portion, that is, the imaging area interposed therebetween. Here, the X-ray generator 311 and the X-ray sensor 312 may irradiate and receive an X-ray beam penetrating the entire imaging area or may irradiate and receive an X-ray beam penetrating a part of the imaging area. The X-ray generator 311 and the X-ray sensor 312 acquire X-ray frame data in various directions while moving along a predetermined locus by the driver 313, thereby securing a plurality of X-ray frame data including the first and second groups of X-ray frame data through a single scan sequence.

Further, a plurality of X-ray frame data is stored in the storage 330.

The image processor 322 reconstructs the cephalometric X-ray image and the tomographic X-ray image by using the first and second groups of X-ray frame data constituted by at least a part of a plurality of X-ray frame data, and stores the same in the storage 330. Here, the cephalometric X-ray image and the tomographic X-ray image may show the same magnification.

For the cephalometric X-ray image, the image processor 322 may connect X-ray frame data in the same direction passing through the entire imaging area or X-ray frame data in the same direction, each of which transmits a portion of the imaging area, over the entire imaging area, and for the tomographic X-ray image, the image processor may reconstruct the X-ray frame data in multiple directions passing through the at least one image layer with a predetermined tomosynthesis algorithm. The image processor 322 may reconstruct a plurality of tomographic X-ray images displayed through the partial image display part according to a user's selection in advance and store them in the storage 330.

Further, the image processor 322 may reconstruct tomographic X-ray images of a plurality of image layers substantially corresponding to the entire imaging area and then superimpose the tomographic X-ray images in the same direction to implement the cephalometric X-ray image. In this case, the cephalometric X-ray image is a two-dimensional X-ray image without depth resolution, so there is no reason to distinguish it from a cephalometric X-ray image, in which X-ray frame data in the same direction passing through the entire imaging area or X-ray frame data in the same direction, each of which transmits a portion of the imaging area, are connected over the entire imaging area. Further, for the tomographic X-ray image, the image processor 322 may reconstruct the tomographic X-ray image by acquiring the multi-directional X-ray frame data penetrating at least one image layer and performing a back-projection with the X-ray image data in a predetermined angle range penetrating each point of the image layer into the corresponding image layer. Here, some of the X-ray image data in a predetermined angle range penetrating each point of the image layer may be calculated by interpolating another X-ray image data, and as in the above description, a tomographic X-ray image reconstructed in this manner can exhibit excellent depth resolution compared to a tomographic X-ray image by a general tomosynthesis algorithm.

The viewer module 323 displays the reconstructed cephalometric X-ray image on the background image display part 11, and displays the reconstructed tomographic X-ray image on the partial image display part 21. Here, the tomographic X-ray image may be displayed arbitrarily by default or by the user's choice. In other words, before the display of the tomographic X-ray image or after the display of any tomographic X-ray image, the user can select the position, angle, quantity, or thickness of at least one image layer, and the viewer module 322 displays the tomographic X-ray image of the image layer according to the user's selection on the partial image display part 21 or changes the same.

Further, the viewer module 322 may adjust the size, position, shape or quantity of the partial image display part 21 according to the user's selection, and when necessary, may display an indicator indicating the relative positional relationship of the tomographic X-ray image in the cephalometric X-ray image.

Meanwhile, when it is intended to see the subject's head structure through the X-ray image display apparatus according to the present invention, that is, when the first X-ray image is the cephalometric X-ray image, the image layer of the tomographic X-ray image may be passing through or near the maxillary sinus.

For reference, in normal ENT diagnosis, the cephalometric X-ray image is usually used to identify the head structure and to diagnose the maxillary sinus and surrounding tissues, but due to the characteristics of the two-dimensional X-ray image, it is difficult to identify the maxillary sinus and the surrounding tissues by being overlapped with the skull.

Figure 22:
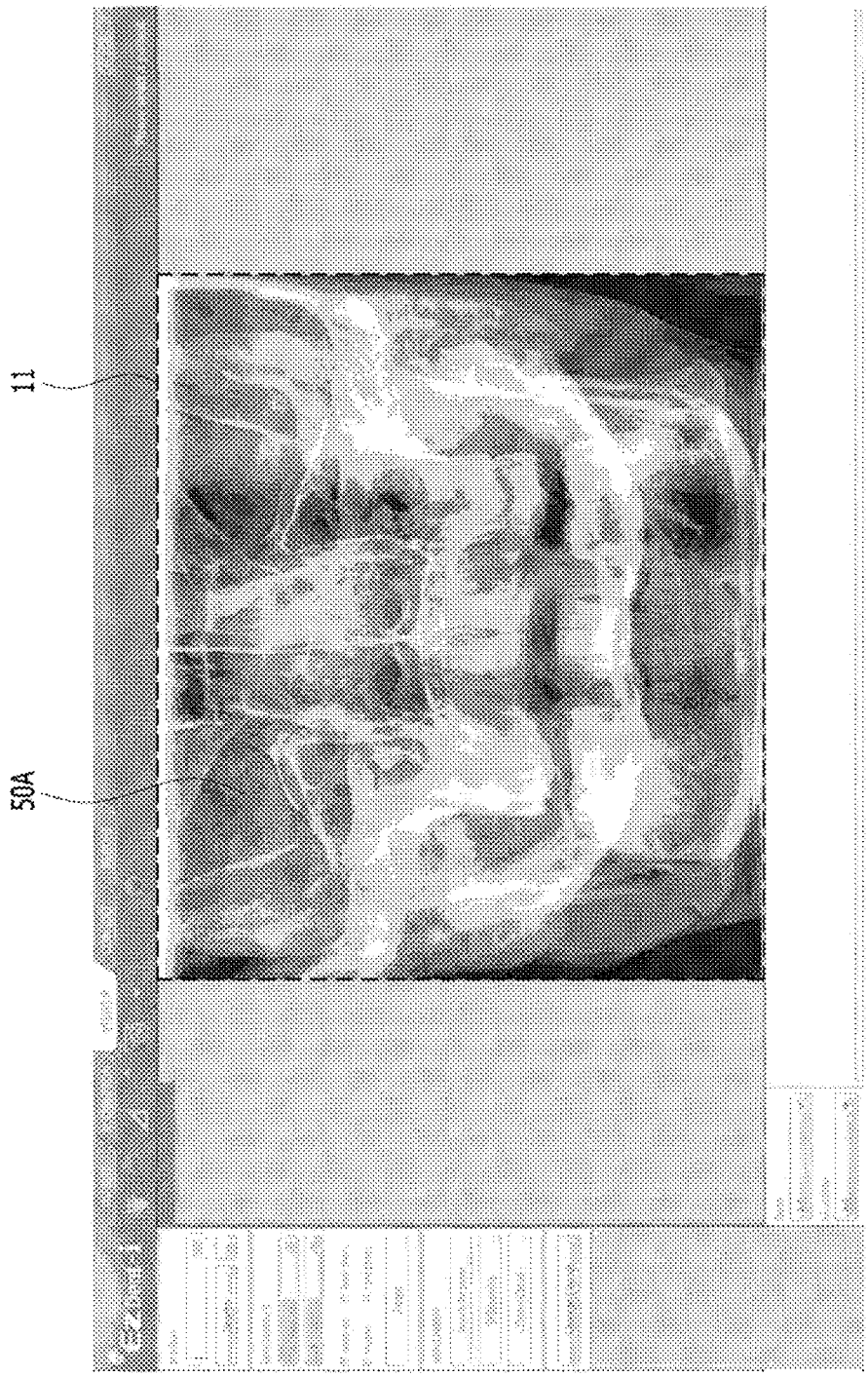
FIG. 22 shows a comparative example of the display screen of FIG. 21.

FIG. 22 shows a comparative example of the display screen of FIG. 21, wherein the first X-ray image—the cephalometric X-ray image is only displayed on the background image display part 11.

As shown in FIG. 22, due to the characteristics of the two-dimensional X-ray image, the cephalometric X-ray image is displayed with the skull in an overlapped manner, which is the same in the maxillary sinus. On the contrary, in the tomographic X-ray image of the partial image display part 21 in FIG. 21, it can be seen that the overlapping phenomenon of the skull has been removed from the maxillary sinus.

Accordingly, the X-ray image display apparatus according to the present invention is capable of allowing the head structure to be identified through the cephalometric X-ray image displayed on the background image display part 11 and capable of providing an X-ray image suitable for diagnostic purposes through a tomographic X-ray image of the maxillary sinus and a part thereof displayed on the partial image display part 21. However, the cephalometric X-ray image and the tomographic X-ray image provided through the X-ray image display apparatus according to the present invention are not limited thereto.

In addition, the X-ray image processor according to the present invention can provide various functions for user convenience, all of which are within the scope of the present invention as applied to the technical idea of the present invention.

Although a preferred embodiment of the present invention has been described for illustrative purposes, those skilled in the art will appreciate that various modifications, additions and substitutions are possible, without departing from the scope and spirit of the invention as disclosed in the accompanying claims.

DESCRIPTION OF REFERENCE CHARACTERS
OF IMPORTANT PARTS

10: first panoramic X-ray image
11: background image display part
15, 15a, 15b: first image layer
20: second panoramic X-ray image
21: partial image display part
25, 25a, 25b: second image layer
31: indicator display part

INDUSTRIAL APPLICABILITY

The present disclosure relates to an X-ray image display apparatus and a method for X-ray image display, and is applicable to a panoramic X-ray image display apparatus and an X-ray imaging apparatus including the same, and the like.

The invention claimed is:
1. An X-ray image display apparatus, comprising:
a storage configured to store a plurality of X-ray frame data of a subject;
an image processor configured to reconstruct a first X-ray image by using a first group of X-ray frame data constituted by at least a portion of the plurality of X-ray frame data, and to reconstruct a second X-ray image by using a second group of X-ray frame data constituted by at least a portion of the plurality of X-ray frame data;
a display configured to provide a screen; and
a viewer module configured to display a background image display part and a partial image display part disposed at a portion of the background image display part on the screen, to display the first X-ray image on the background image display part, and to display a portion of the second X-ray image corresponding to the first X-ray image on the partial image display part,
wherein the first group of X-ray frame data and the second group of X-ray frame data are at least partially different from each other, and the second X-ray image is a tomographic X-ray image of at least one image layer,
wherein the two-dimensional X-ray image is a two-dimensional cephalometric X-ray image.
2. The apparatus of claim 1, further comprising:
an X-ray generator and an X-ray sensor facing each other with the subject interposed therebetween; and
a driver configured to move the X-ray generator and the X-ray sensor along a predetermined locus,
wherein the plurality of X-ray frame data is obtained through a single scan sequence of both the X-ray generator and the X-ray sensor.
3. The apparatus of claim 1, further comprising:
an input unit for user manipulation,
wherein the image processor is configured to modify at least one of quantity, position, shape, angle, and thickness of the at least one image layer by the user manipulation and reconstruct the second X-ray image of the modified image layer, and
the viewer module is configured to display a portion of the second X-ray image of the modified image layer corresponding to the first X-ray image on the partial image display part.
4. The apparatus of claim 1, further comprising:
an input unit for user manipulation,
wherein the image processor is configured to modify at least one of position, size, shape, and quantity of the partial image display part by the user manipulation.

5. The apparatus of claim 1, further comprising:
an input unit for user manipulation,
wherein the image processor is configured to reconstruct a plurality of second X-ray images different from each other in at least one of quantity, position, shape, angle, and thickness of the at least one image layer, and
the viewer module is configured to display one of the plurality of second X-ray images on the partial image display part according to the user manipulation.

6. The apparatus of claim 1, wherein the image processor is configured to generate an X-ray frame data group penetrating each point of the at least one image layer in a predetermined angle range by using the second group of X-ray frame data, and to reconstruct the second X-ray image by using the X-ray frame data group.

7. The apparatus of claim 6, wherein the image processor is configured to perform a back-projection with the X-ray frame data group onto the each point of the at least one image layer.

8. The apparatus of claim 1, wherein the first X-ray image is a first tomographic X-ray image of at least one first image layer, the second X-ray image is a second tomographic X-ray image of at least one second image layer, and the first and second image layers are different from each other in at least one of quantity, position, shape, angle, and thickness.

9. The apparatus of claim 8, wherein the first and second tomographic X-ray images are panoramic X-ray images.

10. The apparatus of claim 1, wherein the at least one image layer is within the two-dimensional X-ray image.

11. A method for displaying an X-ray image of an X-ray image display apparatus, in which the X-ray image display apparatus includes a storage, an image processor, a display, and a viewer module, the method comprising:
storing a plurality of X-ray frame data of a subject in the storage;
reconstructing a first X-ray image by using a first group of X-ray frame data constituted by at least a portion of the plurality of X-ray frame data by the image processor, and reconstructing a second X-ray image by using a second group of X-ray frame data constituted by at least a portion of the plurality of X-ray frame data by the image processor; and
displaying a background image display part and a partial image display part disposed at a portion of the background image display part on a screen of the display by the viewer module, displaying the first X-ray image on the background image display part by the viewer module, and displaying a portion of the second X-ray image corresponding to the first X-ray image on the partial image display part by the viewer module,
wherein the first group of X-ray frame data and the second group of X-ray frame data are at least partially different from each other, and the second X-ray image is a tomographic X-ray image of at least one image layer,
wherein the two-dimensional X-ray image is a two-dimensional cephalometric X-ray image.

* * * * *